(12) United States Patent
Sung et al.

(10) Patent No.: US 11,786,594 B2
(45) Date of Patent: Oct. 17, 2023

(54) SPIKY METAL ORGANIC FRAMEWORK, METHOD FOR FABRICATING THEREOF, AND KIT FOR TREATING CANCER

(71) Applicant: NATIONAL TSING HUA UNIVERSITY, Hsinchu (TW)

(72) Inventors: Hsing-Wen Sung, Hsinchu (TW); Po-Ming Chen, New Taipei (TW); Wen-Yu Pan, Taipei (TW); Yang-Bao Miao, Hsinchu (TW); Po-Kai Luo, Chiayi County (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 196 days.

(21) Appl. No.: 17/205,732

(22) Filed: Mar. 18, 2021

(65) Prior Publication Data

US 2021/0393781 A1 Dec. 23, 2021

(30) Foreign Application Priority Data

Jun. 18, 2020 (TW) .................................. 109120643

(51) Int. Cl.
*A61K 41/00* (2020.01)
*C07F 5/06* (2006.01)
*C07F 15/00* (2006.01)
*A61K 39/395* (2006.01)
*A61N 5/06* (2006.01)
*A61K 9/14* (2006.01)

(52) U.S. Cl.
CPC ............ *A61K 41/0057* (2013.01); *A61K 9/14* (2013.01); *A61K 39/3955* (2013.01); *A61N 5/062* (2013.01); *C07F 5/069* (2013.01); *C07F 15/0053* (2013.01); *A61N 2005/066* (2013.01); *A61N 2005/0659* (2013.01); *A61N 2005/0661* (2013.01); *A61N 2005/0662* (2013.01)

(58) Field of Classification Search
CPC .. A61K 41/0057; A61K 9/14; A61K 39/3955; A61N 5/062; A61N 2005/0659; A61N 2005/066; A61N 2005/0661; A61N 2005/0662; C07F 5/069; C07F 15/0053
See application file for complete search history.

*Primary Examiner* — Robert S Cabral
(74) *Attorney, Agent, or Firm* — Joseph C. Zucchero; Carolyn S. Elmore; Elmore Patent Law Group, P.C.

(57) ABSTRACT

A spiky metal organic framework is provided in the present disclosure. The spiky metal organic framework is formed by a coordination reaction between at least one metal ion and an organic ligand, and includes a body and a plurality of spike-like structures. The body is a spherical shape, and a particle size of the body is 1 μm to 3 μm. The spike-like structures are distributed on a surface of the body, a diameter of each spike-like structure is 15 nm to 35 nm, and a length of each spike-like structure is 250 nm to 400 nm.

8 Claims, 30 Drawing Sheets

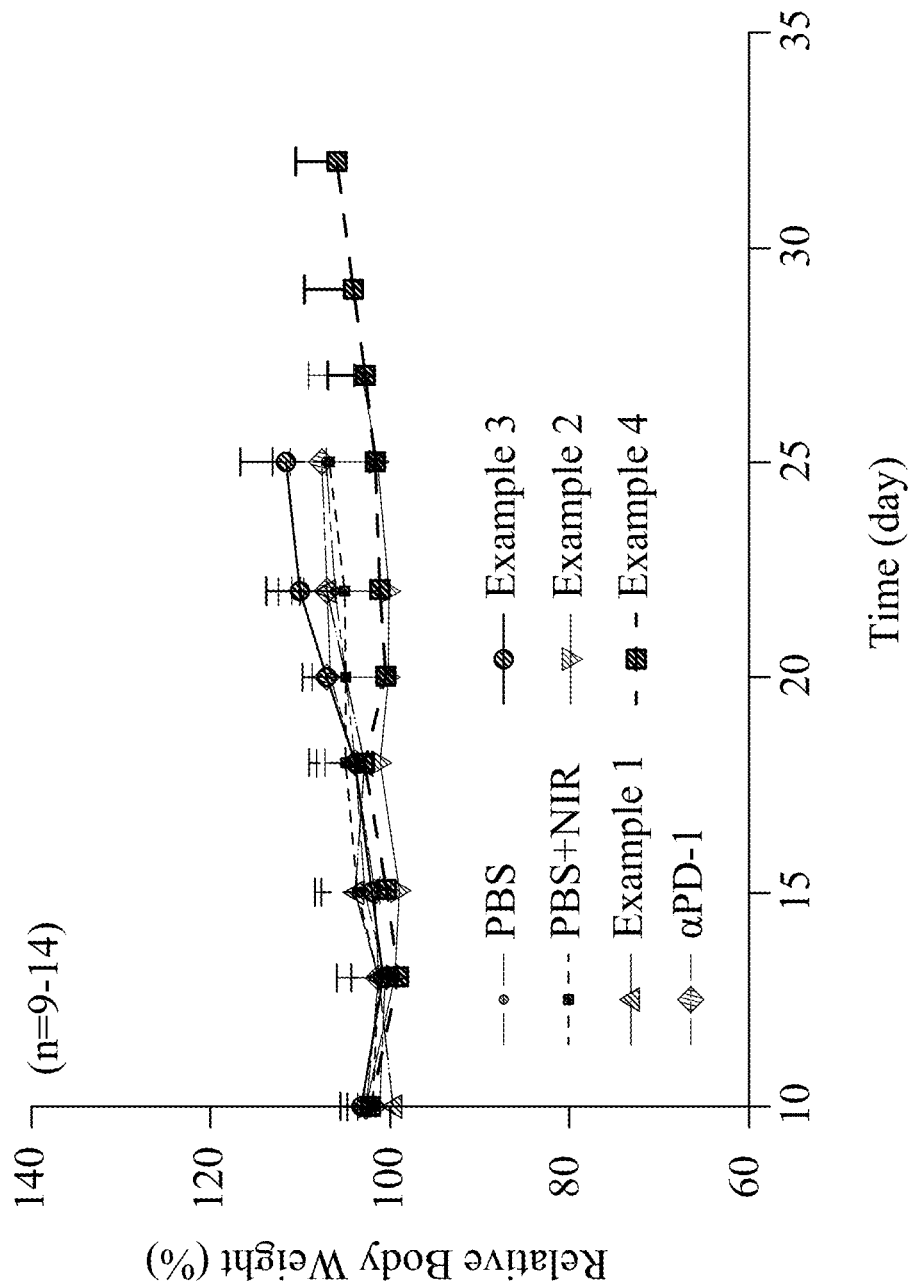

US 11,786,594 B2

SPIKY METAL ORGANIC FRAMEWORK, METHOD FOR FABRICATING THEREOF, AND KIT FOR TREATING CANCER

RELATED APPLICATIONS

This application claims priority to Taiwan Application Serial Number 109120643, filed Jun. 18, 2020, which is herein incorporated by reference.

BACKGROUND

Technical Field

The present disclosure relates to a metal organic framework, a method for fabricating thereof and a kit including the metal organic framework. More particularly, the present disclosure relates to a metal organic framework with a special physical form, a method for fabricating thereof and a kit including the metal organic framework.

Description of Related Art

Cancer, also known as malignancy, is a state of abnormal proliferation of cells, and these proliferating cells may invade other parts of the body as a disease caused by a malfunction in the control of cell division and proliferation. The number of people suffering from cancer worldwide has a growing trend. Cancer is one of the top ten causes of death and has been the top ten causes of death for twenty-seven consecutive years.

Bacteria-mediated tumor therapy (BMTT) is known to retard neoplasm growth that is caused by crosstalk between microbes and the host tumor microenvironment. Bacteria exhibit a number of immune-mediated characteristics that modulate the tumor microenvironment and thus are regarded as antitumor agents for cancer immunotherapy. Based on the relevant literature, injecting specific bacteria into tumors can cause the infiltration of immune cells, such as macrophages, which can be activated locally through inflammasome pathways, secreting pro-inflammatory cytokines, such as interleukin-1β (IL-1β), suppressing tumor growth. The injected bacteria in the tumor tissue can activate the defense mechanism of the host, increasing the number of tumor-specific cytotoxic T cells, which destroy tumor cells. Moreover, bacterial injections can induce necrotic cells to generate heat shock proteins, such as HSP70, resulting in the maturation of antigen presenting cells (APCs), which participate extensively in antitumor activities. The antitumor response of bacteria is also likely to be associated with the adjuvant effect of their microbial-associated molecular pattern molecules, including fimbriae and lipopolysaccharide.

Although BMTT is regarded as effective, the use of bacteria in antitumor treatment has never become a routine clinical practice because of the risk that bacterial toxins cause infections. The development of an anti-tumor immune response that can imitate BMTT without adverse toxin side effects can become an important development target with potential in current tumor treatment methods.

SUMMARY

According to one aspect of the present disclosure, a spiky metal organic framework is formed by a coordination reaction between at least one metal ion and an organic ligand, and includes a body and a plurality of spike-like structures. The body is a spherical shape, and a particle size of the body is 1 μm to 3 μm. The spike-like structures are distributed on a surface of the body, a diameter of each spike-like structure is 15 nm to 35 nm, and a length of each spike-like structure is 250 nm to 400 nm.

According to another aspect of the present disclosure, a method for fabricating the abovementioned spiky metal organic framework includes steps as follows. A mixed solution is provided, a firing step is performed and the spiky metal organic framework is collected. The mixed solution includes the at least one metal ion, the organic ligand and a solvent. In the firing step, the mixed solution is calcined at a calcining temperature for a calcining time to obtain the spiky metal organic framework, wherein the calcining temperature is 160° C. to 200° C., and the calcining time is 8 hours to 24 hours.

According to still another aspect of the present disclosure, a kit for treating cancer is provided. The kit for treating cancer includes the spiky metal organic framework according to the aforementioned aspect and a light supply device for irradiating the spiky metal organic framework.

BRIEF DESCRIPTION OF THE DRAWINGS

The present disclosure can be more fully understood by reading the following detailed description of the embodiment, with reference made to the accompanying drawings as follows:

FIG. 15A shows weight curves of the Balb/c tumor mice in different treatment groups.

DETAILED DESCRIPTION

The following descriptions of particular embodiments and examples are provided by way of illustration and not by way of limitation. Those skilled in the art will readily recognize a variety of noncritical parameters that could be changed or modified to yield essentially similar results.

Unless otherwise stated, the meanings of the scientific and technical terms used in the specification are the same as those of ordinary skill in the art. Furthermore, the nouns used in this specification are intended to cover the singular and plural terms of the term unless otherwise specified.

The term "individual" or "patient" refers to an animal that is capable of administering a spiky metal organic framework and/or a kit for treating cancer of the present disclosure. Preferably, the animal is a mammal.

The term "cancer" refers to a non-solid tumor or a solid tumor. For example, cancer includes, but is not limited to, blood cancer, lymphoma, diaphyseal osteosarcoma, multiple myeloma, testicular cancer, thyroid cancer, prostate cancer, laryngeal cancer, cervical cancer, nasopharyngeal cancer, breast cancer, colorectal cancer, pancreatic cancer, head and neck cancer, esophageal cancer, rectal cancer, lung cancer, liver cancer, brain cancer, melanoma or skin cancer.

The term "about" means that the actual value falls within the acceptable standard error of the average, as determined by person having ordinary skill in the art. The scope, number, numerical values, and percentages used herein are modified by the term "about" unless example or otherwise stated. Therefore, unless otherwise indicated, the numerical values or parameters disclosed in the specification and the claims are approximate values and can be adjusted according to requirements.

Figure 1:
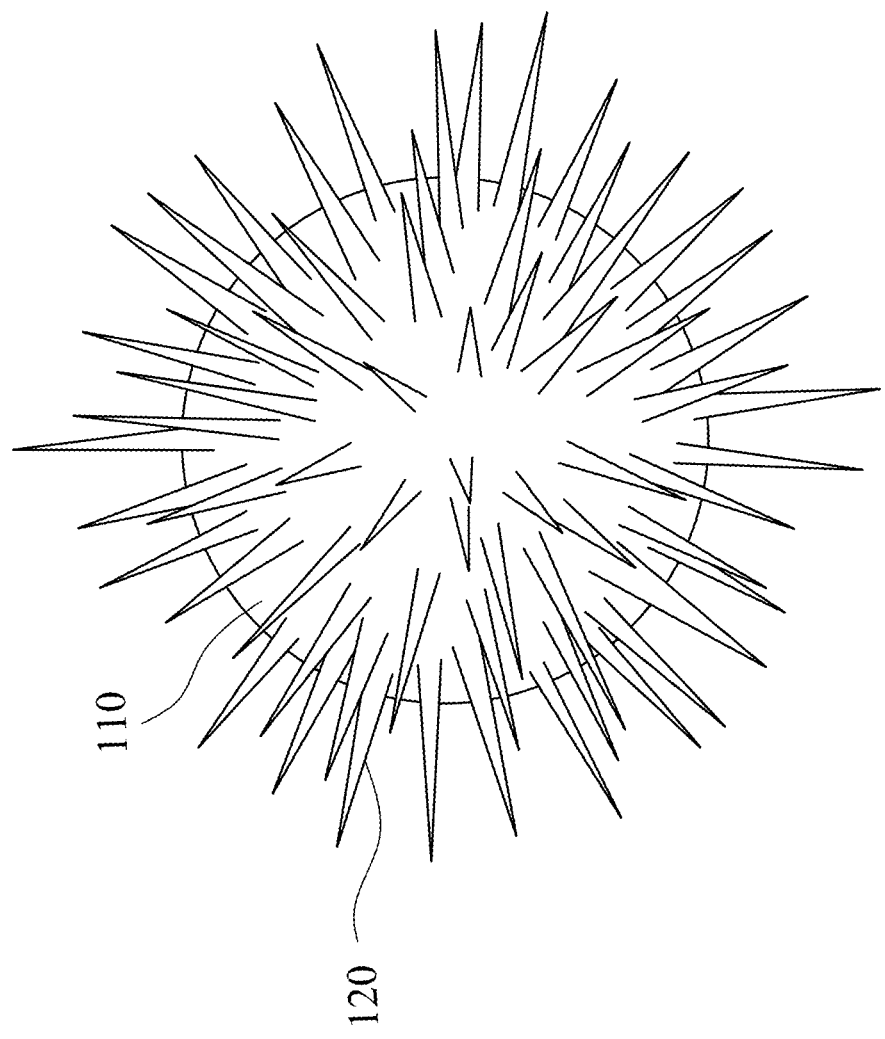
FIG. 1 is a structural schematic view showing a spiky metal organic framework according to the present disclosure.

Please refer to FIG. 1, which is a structural schematic view showing a spiky metal organic framework 100 according to the present disclosure. The spiky metal organic framework 100 is formed by a coordination reaction between at least one metal ion and an organic ligand. As shown in FIG. 1, the spiky metal organic framework 100 includes a body 110 and a plurality of spike-like structures 120. The body 110 is a spherical shape, and a particle size of the body 110 is 1 μm to 3 μm. The spike-like structures 120 are distributed on a surface of the body 110, a diameter of each spike-like structure 120 is 15 nm to 35 nm, and a length of each spike-like structure 120 is 250 nm to 400 nm.

Furthermore, the at least one metal ion can be aluminum ion, ruthenium ion, cobalt ion, iron ion or zinc ion, and the organic ligand can be 2-aminoterephthalic acid, terephthalic acid or trimesic acid.

Figure 2:
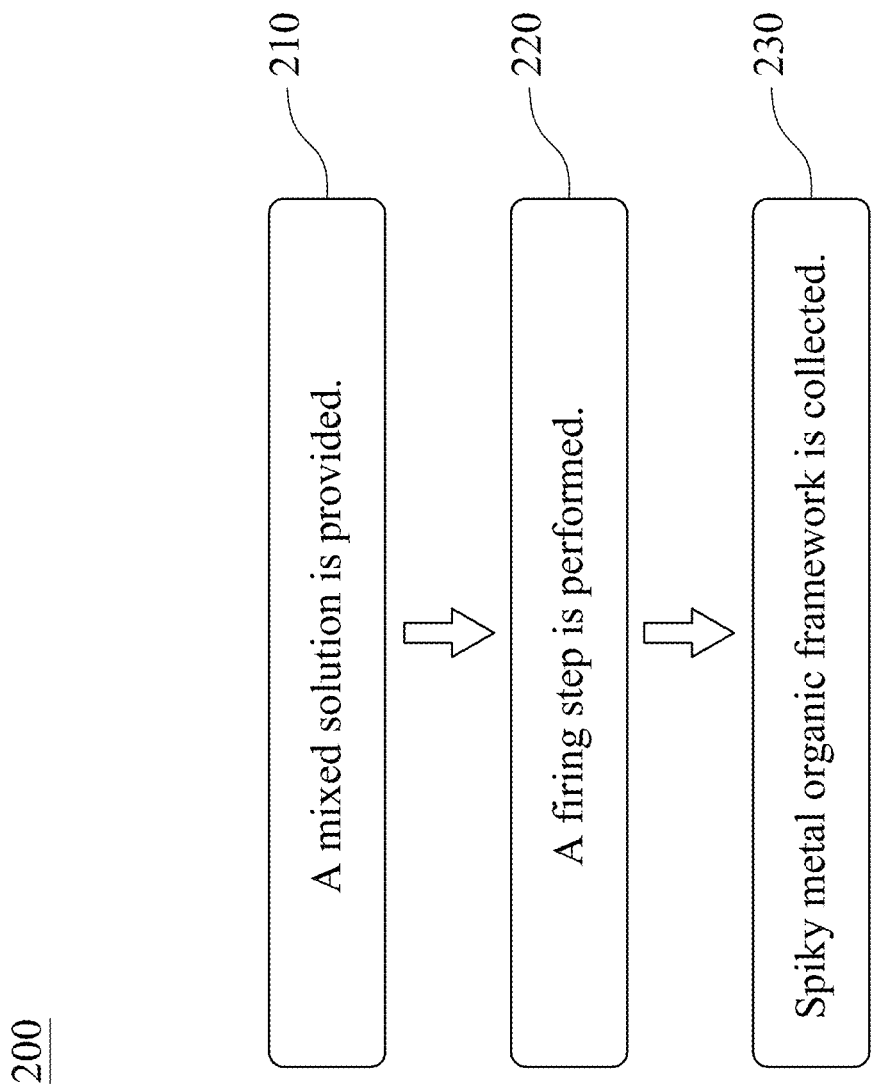
FIG. 2 is a flow chart showing a method for fabricating the spiky metal organic framework according to the present disclosure.

Please refer to FIG. 2, which is a flow chart showing a method for fabricating the spiky metal organic framework 200 according to the present disclosure. The method for fabricating the spiky metal organic framework 200 includes Step 210, Step 220 and Step 230.

In Step 210, a mixed solution is provided. The mixed solution includes the at least one metal ion, the organic ligand and a solvent. The at least one metal ion can be aluminum ion, ruthenium ion, cobalt ion, iron ion or zinc ion. Preferably, the at least one metal ion can be aluminum ion and ruthenium ion, and a mole ratio of the aluminum ion to the ruthenium ion is 2:3 to 6:1. The organic ligand can be 2-aminoterephthalic acid, terephthalic acid or trimesic acid. The solvent can be N,N-dimethylformamide (DMF), water, methanol or ethanol.

In Step 220, a firing step is performed. In the firing step, the mixed solution is calcined at a calcining temperature for a calcining time to obtain the spiky metal organic framework. The calcining temperature is 160° C. to 200° C., and the calcining time is 8 hours to 24 hours. Preferably, the calcining temperature can be 180° C., and the calcining time can be 10 hours.

In Step 230, the spiky metal organic framework is collected, which can be achieved through steps such as concentration under reduced pressure, centrifugation, filtration, washing or drying.

Accordingly, the spiky metal organic framework of the present disclosure fabricated by the aforementioned method has a structure similar to the appearance of bacteria, so the spiky metal organic framework can imitate the anti-tumor immune response of BMTT. The mechanisms by which the spiky metal organic framework recruits immune cells to the host tumor microenvironment and activates them, converting a whole tumor into an in situ vaccine. In addition, the spiky metal organic framework of the present disclosure does not have exotoxins and endotoxins, so it will not produce adverse side effects. Preferably, when at least one metal ion of the spiky metal organic framework is aluminum ion, the spiky metal organic framework of the present disclosure can be further used as an immune adjuvant to recruit and activate antigen presenting cells (APCs) and to stimulate the proliferation and activation of T cells. When at least one metal ion of the spiky metal organic framework is ruthenium ion, the ruthenium-based complex has light absorption characteristics and excellent photothermal-conversion efficiency, so that the spiky metal organic framework of the present disclosure can be further used as a photothermal agent.

The aforementioned spiky metal organic framework can be cooperated with a light supply device as a kit for treating cancer. A light source of the light supply device can be ultraviolet light (UV), near infrared light (NIR), far infrared light (FIR) or visible light (VIS). The spiky metal organic framework can absorb light energy generated by the light supply device to generate a mild thermal energy and maintain the mild thermal energy. Accordingly, the kit for treating cancer has the dual effects of hyperthermia therapy and immunotherapy, thereby producing a synergistic therapeutic effect, activating the immune mechanism, activating tumor-specific T cell responses to identify tumor antigens, and converting the entire tumor into an in situ individual vaccine. Therefore, the kit for treating cancer can inhibit the growth of the original tumor, develop effective anti-tumor immunity, and greatly improve the efficiency of tumor treatment. Furthermore, the kit for treating cancer can further include an immune checkpoint inhibitor, which can regulate the immunosuppressive pathways of T cells, enhance the systemic anti-tumor immune response, and regulate the immunosuppressive tumor microenvironment to further improve systemic anti-tumor immunity. The immune checkpoint inhibitor can be PD-1 antibody, PD-L1 antibody or CTLA-4 antibody.

The spiky metal organic framework, the method for fabricating thereof and the kit for treating cancer has been described as mentioned above. In the following, reference will now be made in detail to the present embodiments of the present disclosure, experiments and examples of which are illustrated in the accompanying drawings. The accompanied effects of the spiky metal organic framework and the kit for treating cancer disclosed in the experiments and the examples for demonstrating the effect and the mechanism of the spiky metal organic framework and the kit for treating cancer. However, the present disclosure is not limited thereto.

EXPERIMENTS AND EXAMPLES

I. The Spiky Metal Organic Framework of the Present Disclosure and the Method for Fabricating Thereof 1.1 Fabrication and Structure Analysis of the Spiky Metal Organic Framework Spiky metal organic framework of Example 1 (hereinafter referred to as "Example 1") is first fabricated, and metal organic framework of Comparative Example 1 (hereinafter referred to as "Comparative Example 1") and metal organic framework of Comparative Example 2 (hereinafter referred to as "Comparative Example 2") are fabricated as controls. The at least one metal ion used in Example are aluminum ion and ruthenium ion, the organic ligand used is 2-aminoterephthalic acid, and the solvent used is dimethylformamide. The fabrication process of Example 1 is as follows: 0.4 mmol of aluminum sulfate, 0.1 mmol of ruthenium (III) chloride hydrate, and 0.5 mmol of 2-aminoterephthalic acid are dissolved in 50 mL of N,N-dimethylformamide (DMF) at room temperature to obtain a mixed solution. The mixed solution is transferred to a 50 mL Teflon-lined stainless-steel autoclave and then heat-treated at 180° C. for 10 hours. The synthesized Example 1 is separated by centrifugation at 7,000 rpm for 10 minutes and then washed several times with deionized (DI) water and then ethanol to collect Example 1. Except that the calcining temperatures of Comparative Example 1 and Comparative Example 2 are different from that of Example 1, other fabrication conditions are the same. The calcining temperature of Comparative Example 1 is 120° C., and the calcining temperature of Comparative Example 2 is 240° C. The synthesized metal organic frameworks are observed using a scanning electron microscope (JSM-5600, JEOL Technics) to observe the morphologies of Example 1, Comparative Example 1, and Comparative Example 2.

Figure 3A:
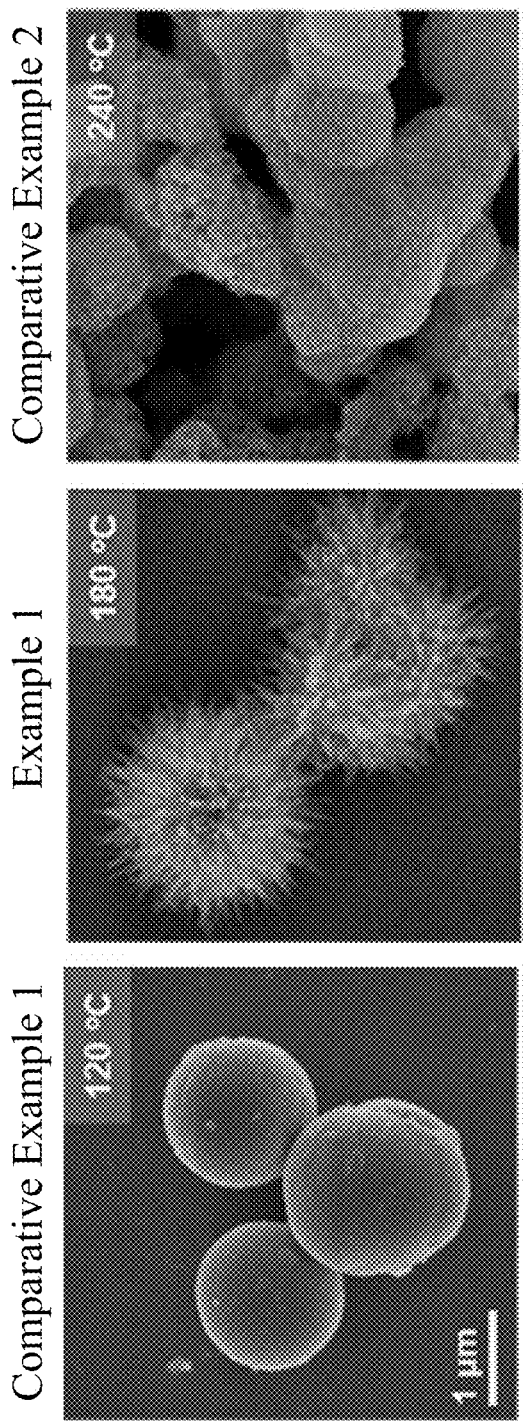
FIG. 3A shows scanning electron microscope images of metal organic frameworks fabricated at different calcining temperatures.

Please refer to FIG. 3A, which shows scanning electron microscope images of the metal organic frameworks fabricated at different calcining temperatures. In FIG. 3A, Comparative Example 1 synthesized at 120° C. is almost spherical. The spiky metal organic framework of Example 1 synthesized at 180° C. has a bacterium-like morphology with a plurality of spike-like structures evenly distributed on a surface of the body. Comparative Example 2 synthesized at 240° C. tends to aggregate and cannot form a single metal organic framework. Both Comparative Example 1 and Example 1 typically have diameters of 1 μm to 3 μm, and are about the average size of most bacteria. they dispersed well in phosphate-buffered saline (PBS) before and after lyophilization. Therefore, in subsequent experiments, Comparative Example 1 is used as a control to evaluate the efficacy of the spiky metal organic framework of the present disclosure.

In addition, the experiment also tested the preparation of the spiky metal organic framework of the present disclosure with different metal ions. The difference between the spiky metal organic framework of Example 5 (hereinafter referred to as "Example 5") and Example 1 is that the at least one metal ion in Example 5 is only aluminum ion. The difference between the spiky metal organic framework of Example 6 (hereinafter referred to as "Example 6") and Example 1 is the mole ratio of aluminum ion and ruthenium ion. In Example 6, the mole ratio of aluminum ion to ruthenium ion is 2:3. The other fabrication processes of Example 5 and Example 6 are same as that of Example 1, and will not be repeated here. The synthesized Example 5 and Example 6 are observed using the scanning electron microscope.

Figure 3B:
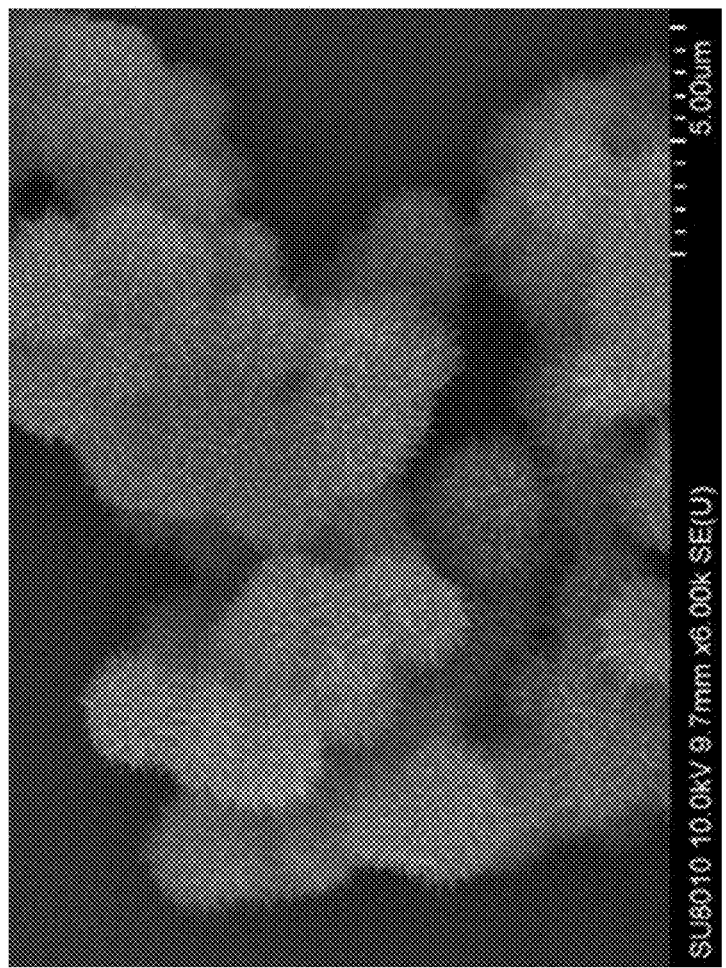
FIGS. 3B and 3C show scanning electron microscope images of metal organic frameworks fabricated by different metal ions.
Figure 3C:
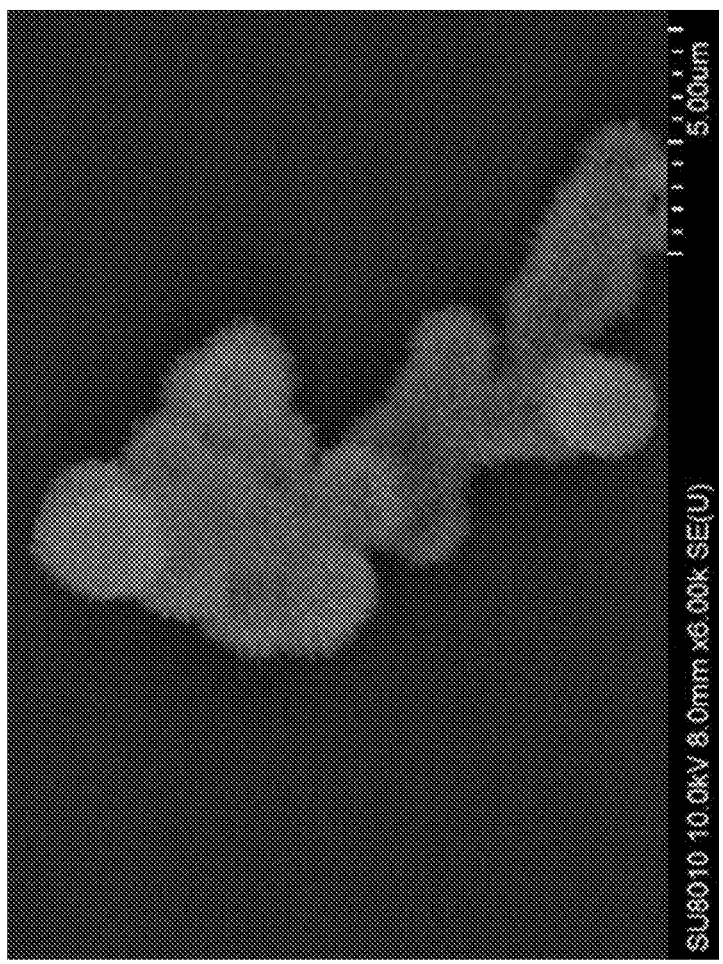

Please refer to FIGS. 3B and 3C, which show scanning electron microscope images of metal organic frameworks fabricated by different metal ions. FIG. 3B shows a scanning electron microscope image of Example 5. FIG. 3C is a scanning electron microscope image of Example 6. In FIG. 3B, Example 5 synthesized with aluminum ion as at least one metal ion has a plurality of spike-like structures evenly distributed on the surface of the body, which can form a bacterium-like form. In FIG. 3C, Example 6 synthesized with aluminum ions and ruthenium ions with a mole ratio of 2:3 has a plurality of spike-like structures evenly distributed on the surface of the body, which can also form a bacterium-like form.

When the metal organic framework is exposed to a physiological fluid with a high concentration of phosphate ions, it is expected that the metal organic framework will gradually degrade because the phosphate ions competitively replace the organic linking group. Comparative Example 1 and Example 1 are incubated in phosphate buffered saline (PBS) to observe the degradation of Example 1 and Comparative Example 1. In addition, the structural changes of Example 1 and Comparative Example 1 are observed by scanning electron microscope at predetermined time points (Day 0, Day 1, Day 2, Day 3, and Day 7), respectively.

Figure 3D:
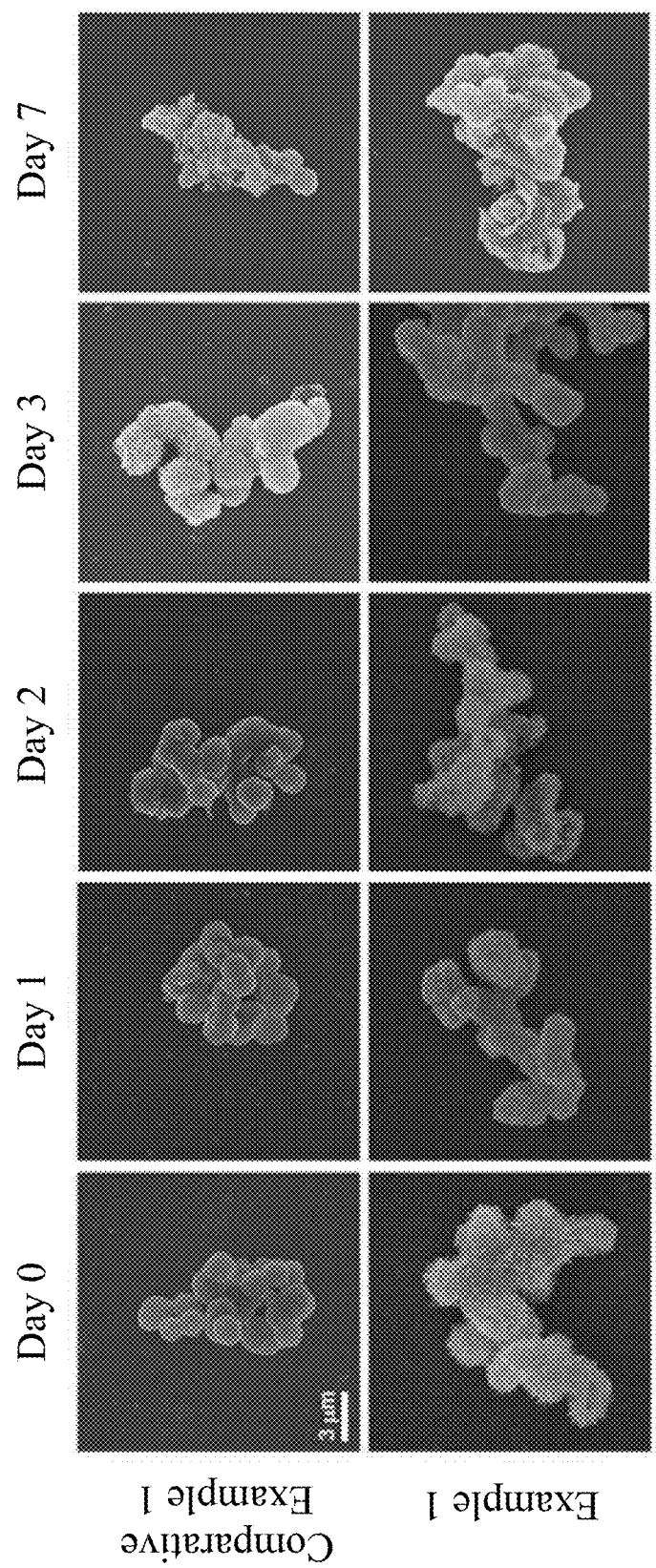
FIG. 3D shows analytical results of degradation according to Example 1 and Comparative Example 1 of the present disclosure.

Please refer to FIG. 3D, which shows analytical results of degradation according to Example 1 and Comparative Example 1 of the present disclosure. In FIG. 3D, both Example 1 and Comparative Example 1 begin to degrade on Day 3, and significant destruction of the incubated Example 1 or Comparative Example 1 is observed on the Day 7. The results indicate the degradability of Example 1 and Comparative Example 1 in a physiological fluid.

The annular dark field (ADF) images and energy dispersive x-ray (EDX) elemental maps of Example 1 and Comparative Example 1 are obtained using Cs-corrected scanning transmission electron microscope (JEOL ARM 200F, JEOL Technics). Elemental analyses of Al and Ru are conducted using inductively coupled plasma mass spectrometry (ICP-MS) (Agilent 7500ce, Agilent Technologies) with the digested materials in aqueous $HNO_3$ solution.

Figure 4A:
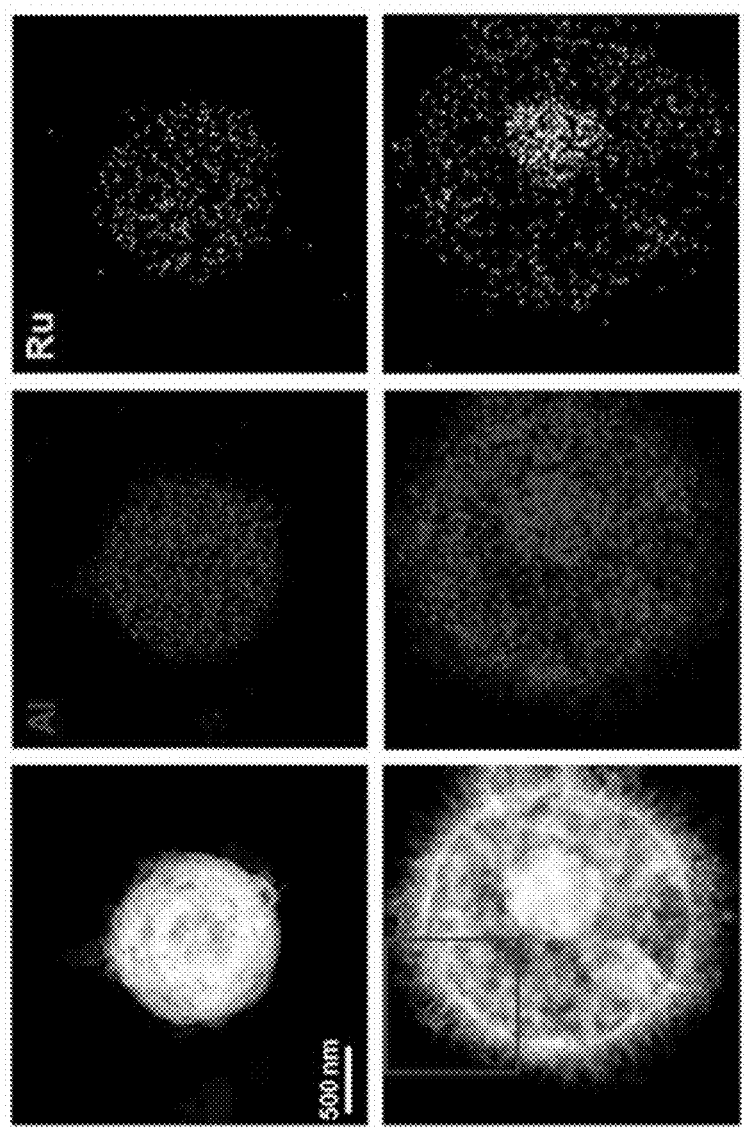
FIGS. 4A and 4B show structural analysis results according to Example 1 and Comparative Example 1 of the present disclosure.
Figure 4B:
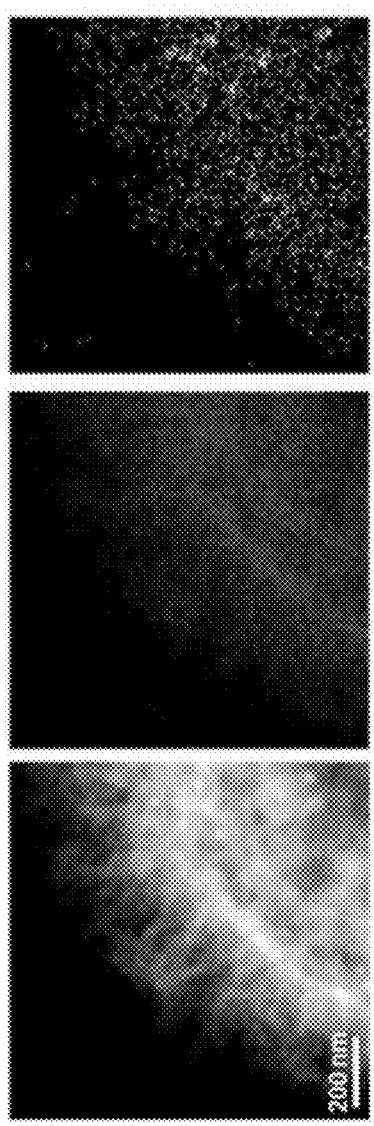
Figure 4C:
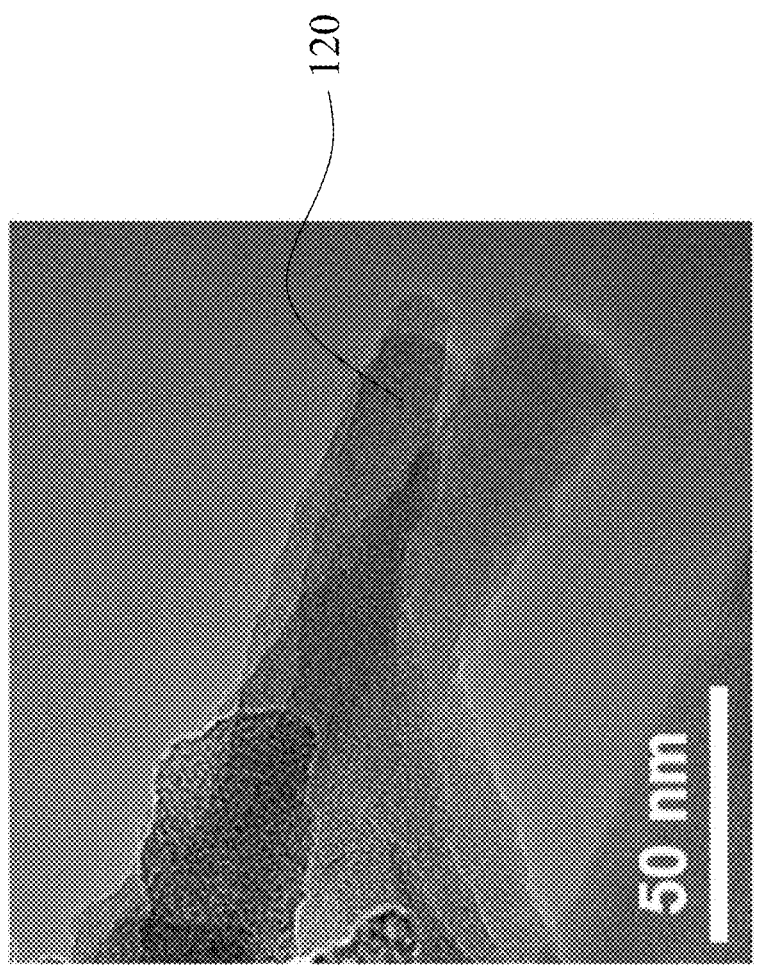
FIG. 4C shows transmission electron microscope image of spike-like structures of the spiky metal organic framework according to Example 1 of the present disclosure.

Please refer to FIGS. 4A, 4B and 4C. FIGS. 4A and 4B show structural analysis results according to Example 1 and Comparative Example 1 of the present disclosure. FIG. 4C shows transmission electron microscope (TEM) image of spike-like structures of the spiky metal organic framework according to Example 1 of the present disclosure. The ADF images in FIG. 4A show that Example 1 has a yolk-shell structure. As revealed by the high-resolution transmission electron microscopic (HRTEM) images in FIG. 4B and the transmission electron microscope image in FIG. 4C, the spike-like structures that protruded from the surface shells of the spiky metal organic framework, which morphologically resembles bacterial pili, has diameters of ca. 25 nm and lengths of ca. 320 nm. Extended exposure of these spike-like structures to an electron beam in TEM do not change their morphology, suggesting that the spike-like structures that are grown on the surfaces of Example 1 are rather rigid. The EDX elemental maps demonstrate that the elemental Al and Ru are well dispersed throughout Example 1 and Comparative Example 1.

Please refer to Table 1 below, which shows the analytical results of ICP-MS. The analytical results show that the Al and Ru contents in Example 1 are similar to those in the Comparative Example 1 ($P>0.05$).

TABLE 1

|  | Al (wt %) | Ru (wt %) |
| --- | --- | --- |
| Comparative Example 1 | 12.6 ± 2.1 | 2.0 ± 1.1 |
| Example 1 | 10.9 ± 1.5 | 2.2 ± 0.5 |

1.2 Analysis of the Characteristics of the Spiky Metal Organic Framework

Both Example 1 and Comparative Example 1 have an evenly distribution of Ru and should be used as a photothermal agent. In order to confirm that the spiky metal organic framework of the present disclosure can absorb light energy to generate heat energy, and maintain a temperature greater than or equal to 39° C. and less than or equal to 50° C., the UV-VIS-NIR absorbance spectra of Example 1 and Comparative Example 1 in PBS are obtained using a SpectraMax M5 Microplate Reader (Molecular Devices, Sunnyvale, Calif., USA). To investigate the photothermal capacities of Example 1 and Comparative Example 1, Example 1 and Comparative Example 1 are dispersed in 48-well plate at various concentrations (150 μg/mL or 600 μg/mL) and then irradiated using an 808 nm NIR laser (Tanyu Tech, Kaohsiung, Taiwan) at a power density of 1.5 W/cm² for 10 minutes. In addition, a group with plain PBS is included as a control. The temperature profiles of these solutions are recorded using a thermocouple (Grand Hand Instrument, Hsinchu, Taiwan).

Figures 5A, 5B:
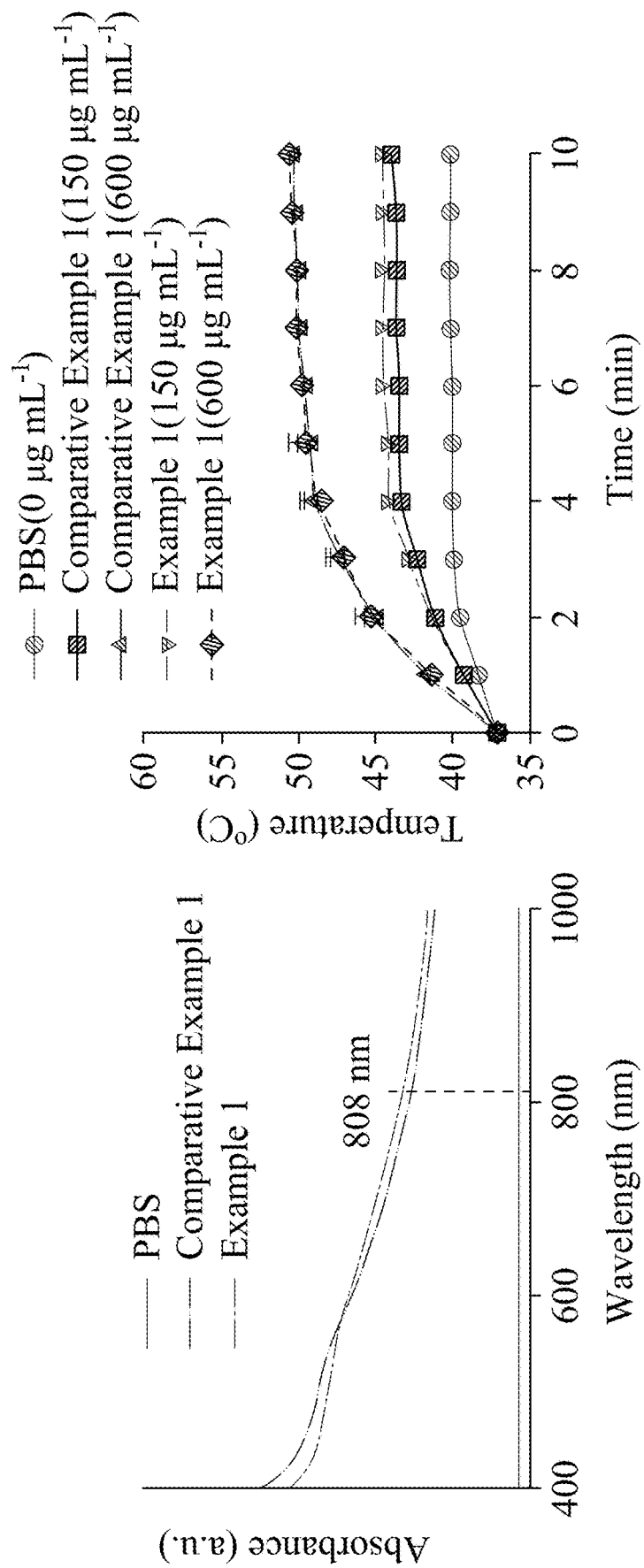
FIG. 5A shows optical absorbance spectra of Example 1 and Comparative Example 1 of the present disclosure.
FIG. 5B shows temperature evolution curves of Example 1 and Comparative Example 1 of the present disclosure following exposure to 808 nm NIR laser.

Please refer to FIGS. 5A and 5B. FIG. 5A shows optical absorbance spectra of Example 1 and Comparative Example 1 of the present disclosure. FIG. 5B shows temperature evolution curves of Example 1 and Comparative Example 1 of the present disclosure following exposure to 808 nm NIR laser. In FIG. 5A, both Example 1 and Comparative Example 1 have similar UV-VIS-NIR absorbance spectra and greater light absorbance than control at 808 nm. In FIG. 5B, compared with the control group, the temperature profile of PBS containing Example 1 is similar to that of PBS containing Comparative Example 1 ($P>0.05$). Exposure to NIR light increased the temperatures of the PBS containing Example 1 or the PBS containing Comparative Example 1 in a concentration-dependent manner, until they reached plateaus within 4 minutes.

The above results indicate that both Example 1 and Comparative Example 1 can function as photothermal agents, effectively converting absorbed optical energy into local heat, mediated by their incorporated Ru. Heat treatment at high temperatures over 55° C. can cause irreparable cell necrosis. To reduce the possibility of the heat-induced elimination of tumor-infiltrating immune cells, all subsequent photothermal heating is carefully regulated to a temperature of about 44° C. The heat-induced cell damage at relatively low temperatures (41° C.-45° C.) is sublethal and reversible.

1.3 Effect of the Spiky Metal Organic Framework on Cytotoxicity and its Application in Hyperthermia Therapy Furthermore, in order to determine the safety and safe dose of the spiky metal organic framework of the present disclosure on tumor cells, different doses of Example 1 are tested for cell viability of the mouse colorectal adenocarcinoma cell line CT26 (hereinafter referred to as "CT26 cells").

The CT26 cells are cultured in DMEM (Dulbecco's modified Eagle's medium) medium containing 10% fetal bovine serum (FBS) and placed in a 37° C., 5% $CO_2$ incubator. The cell viability is determined by the Cell Titer-Glo assay. CT26 cells are co-cultured with Example 1 or Comparative Example 1 at various concentrations (50, 100, 150 and 200 μg/mL), untreated CT26 cells are included as a control. The detailed procedures of the experiment are as follows. The CT26 cells are seeded in 96-well plate at a density of $8\times10^4$ cells/well for 24 hours. Then, Example 1 and Comparative Example 1 prepared with different concentrations are co-cultured with CT26 cells at 37° C. for 24 hours. Cell viability is evaluated using a CellTiter-Glo® Luminescent Cell Viability Assay Kit (Promega, Madison).

Figure 5D:
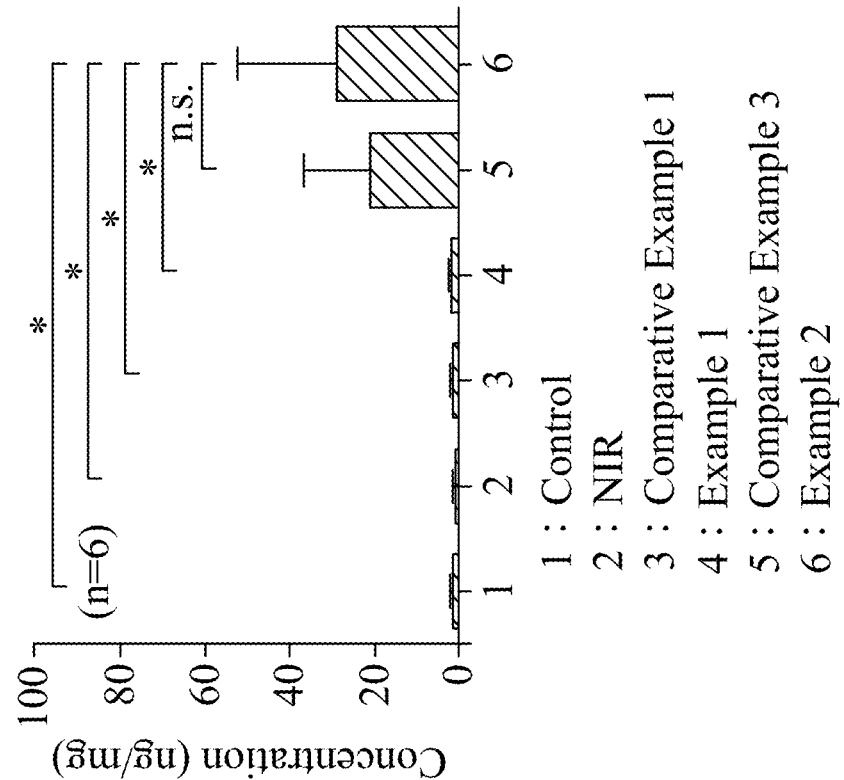
FIG. 5D shows analytical results of HSP70 expression level in CT26 cells after hyperthermia therapy.
Figure 5C:
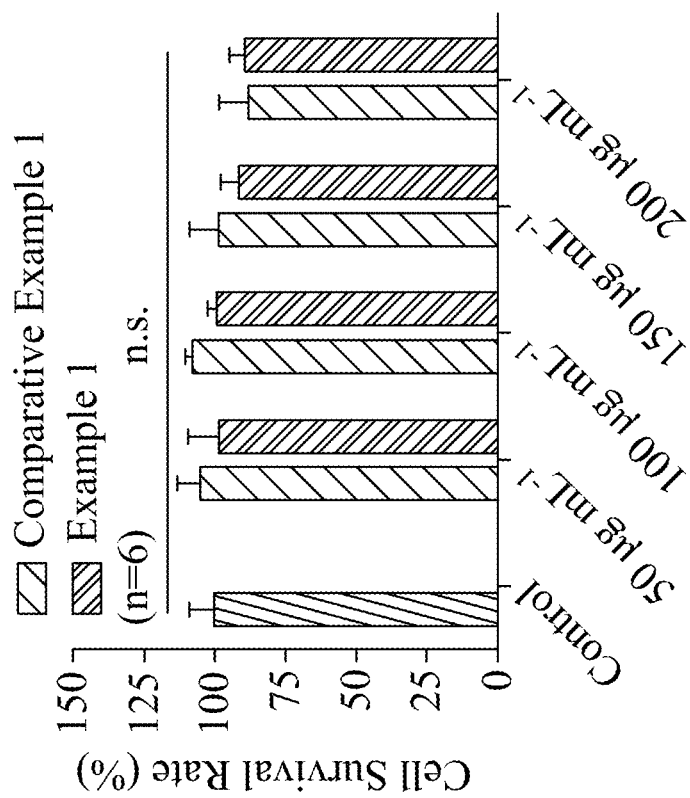
FIG. 5C shows effect of Example 1 and Comparative Example 1 of the present disclosure on survival rates of CT26 cells.

Please refer to FIG. 5C, which shows effect of Example 1 and Comparative Example 1 of the present disclosure on survival rates of CT26 cells. The results show that, no significant difference is detected between the cell viability of CT26 cells treated with Example 1 or Comparative Example 1 at different concentrations and that of untreated control cells ($P>0.05$). The results indicate that the spiky metal organic framework of the present disclosure has a good biocompatibility and low toxicity.

Studies have shown that heat-stressed cancer cells can release heat shock proteins, which may bind to and activate APCs, ultimately initiating adaptive immune responses.

To determine whether heat treatment can induce tumor cell damage and increase their heat shock protein 70 (HSP70) expression levels, the CT26 cells are incubated with Example 1 and then heat-treated using an NIR laser to 44° C. for 10 minutes (hereinafter referred to as "Example 2"). The untreated CT26 cells (hereinafter referred to as "control"), the CT26 cells received only NIR light (hereinafter referred to as "NIR"), the CT26 cells only co-incubated with Example 1 (hereinafter referred to as "Example 1"), the CT26 cells only co-incubated with Comparative Example 1 (hereinafter referred to as "Comparative Example 1"), and the CT26 cells co-incubated with Comparative Example 1 and then heat-treated using an NIR laser to 44° C. for 10 minutes (hereinafter referred to as "Comparative Example 3") are used as control groups. After the aforementioned different treatments, the CT26 cells of each group are cultured at 37° C. for 24 hours. Then, the CT26 cells are lysed and the HSP70 levels in the lysates are measured using a Human/Mouse/Rat Total HSP70/HSPA1A DuoSet IC ELISA Kit (R&D Systems, Minneapolis).

Please refer to FIG. 5D, which shows analytical results of the HSP70 expression level in CT26 cells after hyperthermia therapy. In FIG. 5D, the HSP70 expression level in the CT26 cells of NIR, Example 1 or Comparative Example 1 is similar to that in control ($P>0.05$), whereas the HSP70 expression level in the CT26 cells of Example 2 or Comparative Example 3 is markedly increased, owing to the local elevation of temperature ($P<0.05$).

1.4 The Spiky Metal Organic Framework can be Swallowed by Macrophages and Activate Macrophages Upon invasion by microbes, the functional responses of the phagocytes, such as macrophages, in the host defense system are the phagocytosis of microbes, immunomodulation via the production of various cytokines, and destruction of ingested foreign invaders. The phagocytic capacity of macrophages is affected by the physical parameters of the particles that are taken up, including their size and morphological structure. While the body's macrophages have a size of approximately 10 μm, particles with diameters of 1-3 μm have the highest rate of phagocytosis. To examine the cellular uptake of the spiky metal organic framework of the present disclosure by macrophages, a murine macrophage cell line J774A.1 (hereinafter referred to as "J774A.1 cells") is used in vitro to evaluate the ability of Example 1 and Comparative Example 1 to induce host immune responses. Example 1 and Comparative Example 1 are pre-labeled with Alexa Fluor 633, and untreated macrophages are used as a control group.

The detailed procedures of the experiment are as follows. The J774A.1 cells ($5\times10^5$ cells/mL) are labeled with 1 μM carboxyfluorescein succinimidyl ester (CFSE). The J774A.1 cells are then incubated with Example 1 or Comparative Example 1 (50 μg/mL) that had been pre-labeled with Alexa Fluor 633. Following incubation for predetermined periods (1-24 hours), the J774A.1 cells are collected and washed with PBS. The cellular uptake of the Alexa Fluor 633-labeled Example 1 or Comparative Example 1 is measured using a flow cytometer (BD Accuri C6, BD Biosciences). The flow cytometric data thus obtained are analyzed using FlowJo software (Treestar, Ashland).

Figure 6B:
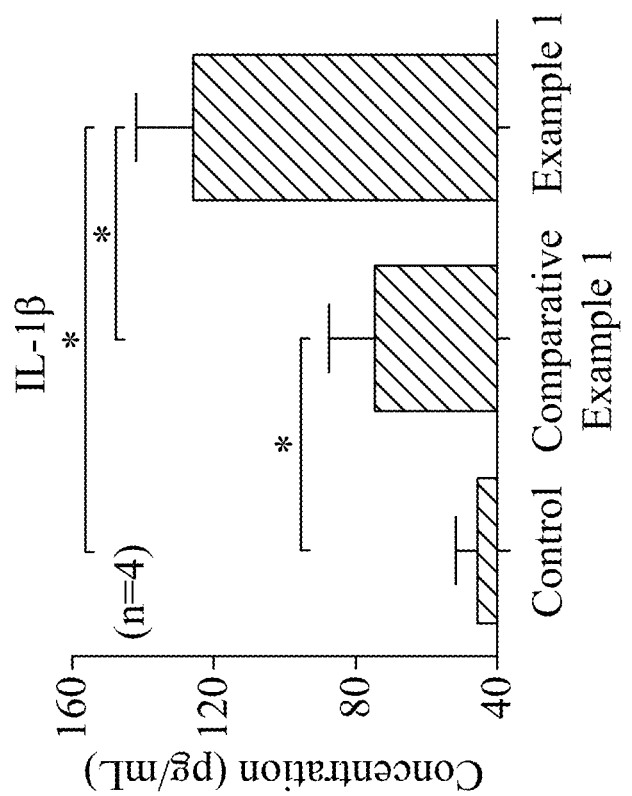
FIG. 6B shows analytical results of levels of pro-inflammatory cytokine secreted by macrophages after treatment in Example 1 or Comparative Example 1 of the present disclosure.
Figure 6A:
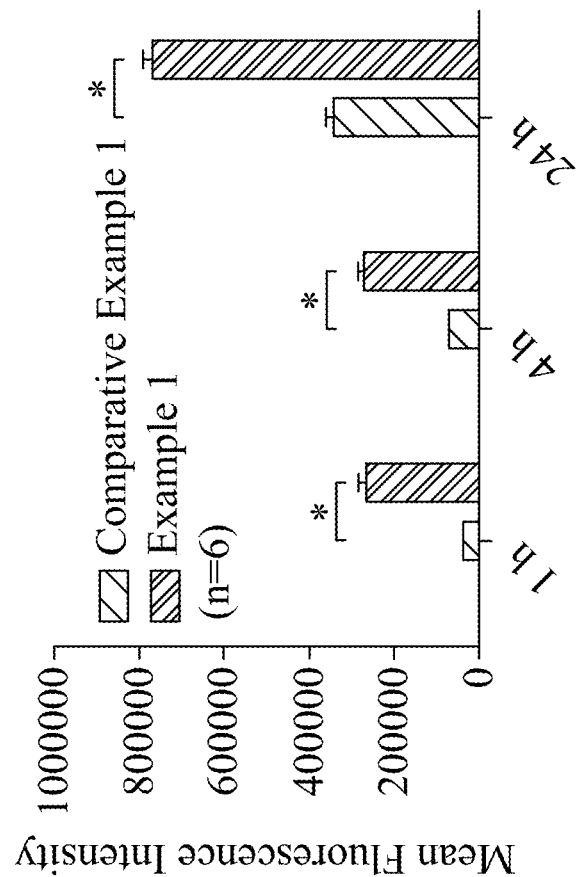
FIG. 6A shows analytical results of macrophage phagocytosis of Example 1 and Comparative Example 1 of the present disclosure.

Please refer to FIG. 6A, which shows analytical results of macrophage phagocytosis of Example 1 and Comparative Example 1 of the present disclosure. In FIG. 6A, the J774A.1 cells treated with Example 1 exhibit a significantly stronger fluorescence signal at 1, 4, and 24 hours, suggesting greater phagocytosis, than the J774A.1 cells treated with Comparative Example 1. This finding reveals that Example 1 is more easily phagocytosed by macrophages than Comparative Example 1, probably because the spike-like structures on Example 1 physically interacted with the cell membranes, increasing their cell adhesion and thus promoting phagocytosis.

The phagocytosis of Example 1 or Comparative Example 1 by macrophages in a tumor microenvironment may cause their maturation by the activation of inflammasome pathways, ultimately upregulating their secretion of pro-inflammatory cytokines, such as IL-1β, which are important in engaging T cell activities. To mimic the conditions of an in vivo encounter with tumor-associated antigens following the injection of Example 1 or Comparative Example 1, macrophages are stimulated by the supernatants that are obtained from culturing CT26 cells that had been treated with Example 1 or Comparative Example 1 under NIR exposure. The levels of IL-1β in the stimulated macrophages that are secreted into the supernatants are analyzed by enzyme-linked immunosorbent assay (ELISA). Untreated macrophages are uses as a control.

Please refer to FIG. 6B, which shows analytical results of levels of pro-inflammatory cytokine secreted by macrophages after treatment in Example 1 or Comparative Example 1 of the present disclosure. In FIG. 6B, the groups that had been treated with Example 1 or Comparative Example 1 exhibit markedly higher levels of IL-1β than the untreated control group ($P<0.05$), suggesting that the Al that is incorporated into Example 1 or Comparative Example 1 effectively induces inflammasome activation in macrophages and thus increased their pro-inflammatory cytokine expression. Notably, Example 1 exhibits a higher expression level of IL-1β than Comparative Example 1 ($P<0.05$), revealing that heat-treated Example 1 may induce stronger immune responses than their Comparative Example 1 counterparts.

1.5 In Vivo Characteristics of the Spiky Metal Organic Framework

Example 1 of the spiky metal organic framework has a larger interaction surface area than Comparative Example 1 of the spherical metal organic framework. Therefore, Example 1 may exhibit stronger adhesion to target surfaces than do Comparative Example 1, possibly prolonging retention of the spiky metal organic framework of the present disclosure in biological tissues.

To determine whether Example 1 could be retained longer than Comparative Example 1 following a single intratumoral injection in mice with subcutaneous CT26 tumors, Balb/c tumor mice are established first. Balb/c mice are subcutaneously inoculated with $1\times10^6$ CT26 cells in their right flanks (primary tumor). Twelve days later, when the tumors had reached sizes of approximately 150 mm$^3$, the Balb/c tumor mice are intratumorally injected with Alexa Fluor 633-labeled Example 1 or Comparative Example 1 (100 μg in 50 μL PBS); the Balb/c tumor mice that had been injected with PBS (50 μL) are the control. To study the intratumoral retention of the injected Example 1 or Comparative Example 1, the biodistributions of their fluorescence are monitored using an IVIS system (Xenogen, Alameda). The fluorescence intensities are obtained using Living Image software (Xenogen).

Figure 7A:
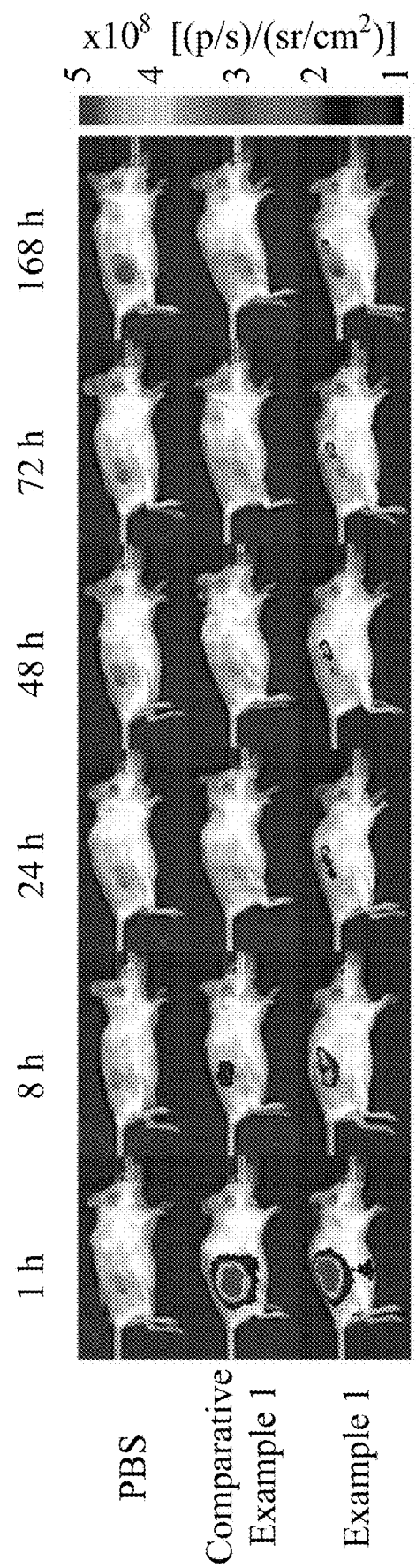
FIG. 7A shows analytical results of biodistribution of Example 1 and Comparative Example 1 of the present disclosure.
Figures 7B, 8:
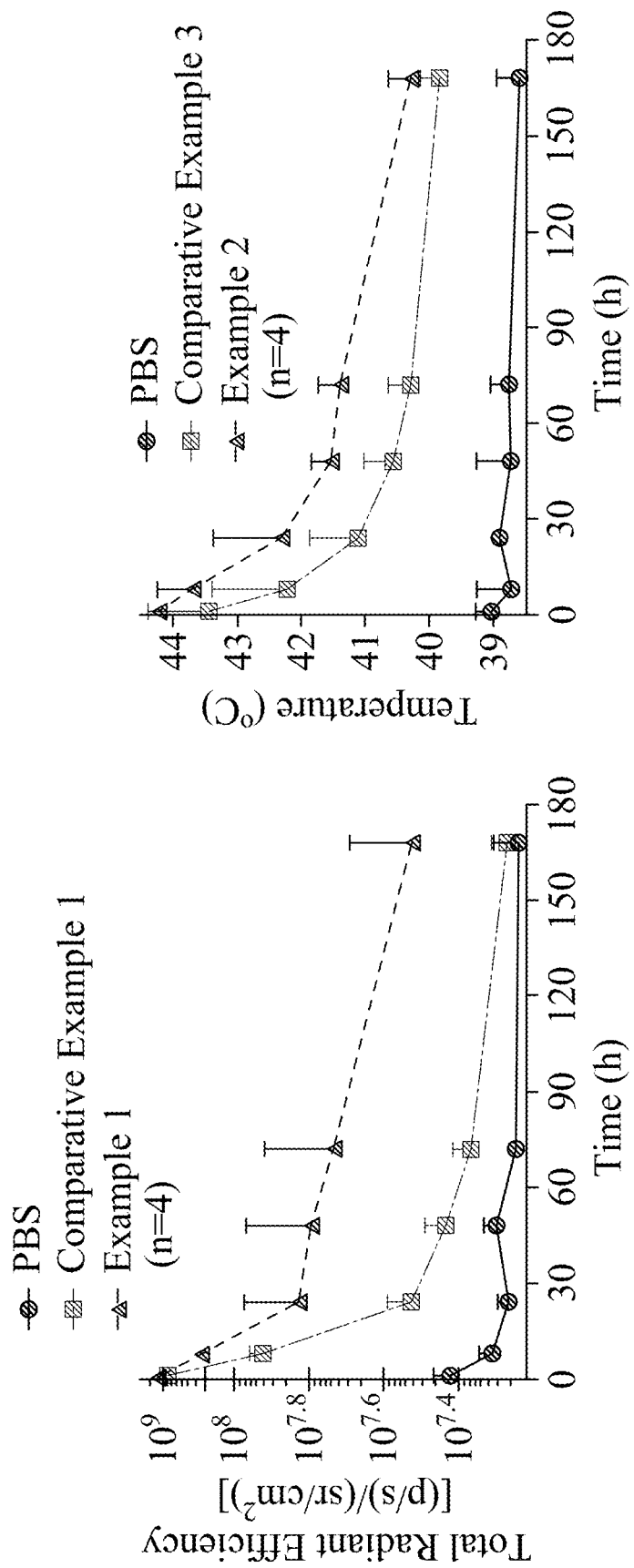
FIG. 7B is a fluorescence intensity statistics graph of FIG. 7A.
FIG. 8 shows analytical results of the metal organic framework used for repeated hyperthermia therapy.

Please refer to FIGS. 7A and 7B. FIG. 7A shows analytical results of biodistribution of Example 1 and Comparative Example 1 of the present disclosure. FIG. 7B is a fluorescence intensity statistics graph of FIG. 7A. In FIGS. 7A and 7B, the group received Example 1 exhibits greater fluorescence intensity than the group received Comparative Example 1. The fluorescence signal from Comparative Example 1 is almost invisible at 24 hours following the intratumoral injection, while that from Example 1 remains detectable for up to seven days, suggesting that Example 1 resides much longer in the tumor tissue than Comparative Example 1, enabling their use in repeated photothermal treatments.

To perform repeated photothermal treatments, tumors that had been injected with Example 1 or Comparative Example 1 are repeatedly exposed to an 808 nm NIR laser at predetermined intervals for 10 minutes each time. The temperature of each tumor is recorded using an IR thermal camera. Please refer to FIG. 8, which shows analytical results of the metal organic framework used for repeated hyperthermia therapy, wherein "Example 2" represents the group treated with Example 1 and then irradiated with 808 nm NIR laser, "Comparative Example 3" represents the group treated with Comparative Example 1 and then irradiated with 808 nm NIR laser, and "PBS" represents the group treated with PBS and then irradiated with 808 nm NIR laser. In FIG. 8, the temperature of tumors in the group that had received PBS+NIR, which served as a control, increased slightly from 35 to 38° C. The temperatures of the tumors in both Example 2 and Comparative Example 3 increased to about 44° C. After repeated exposure to NIR light, the temperature of the tumor of Comparative Example 3 significantly reduced to under 41° C. in 24 hours, whereas the temperature of the tumor of Example 2 remains above 41° C. for up to three days. These results are attributable to the activation by the NIR laser of the administered Example 1, which has a longer residence time within the tumor than that of Comparative Example 1.

The above results indicate that the spiky metal organic framework of the present disclosure has a longer retention time in tumor tissues, can induce greater phagocytosis by macrophages, and induce a stronger immune response than its spherical counterpart. Subsequently, the spiky metal organic framework of the present disclosure is further used in the following in vivo antitumor efficacy studies.

II. Therapeutic Effect of the Spiky Metal Organic Framework and the Kit for Treating Cancer of the Present Disclosure The kit for treating cancer of the present disclosure not only includes the spiky metal organic framework of the present disclosure and the light source device, but also can include immune checkpoint inhibitor to block immune checkpoints, thereby regressing the first tumor and inhibiting tumor recurrence and metastasis.

Figure 9:
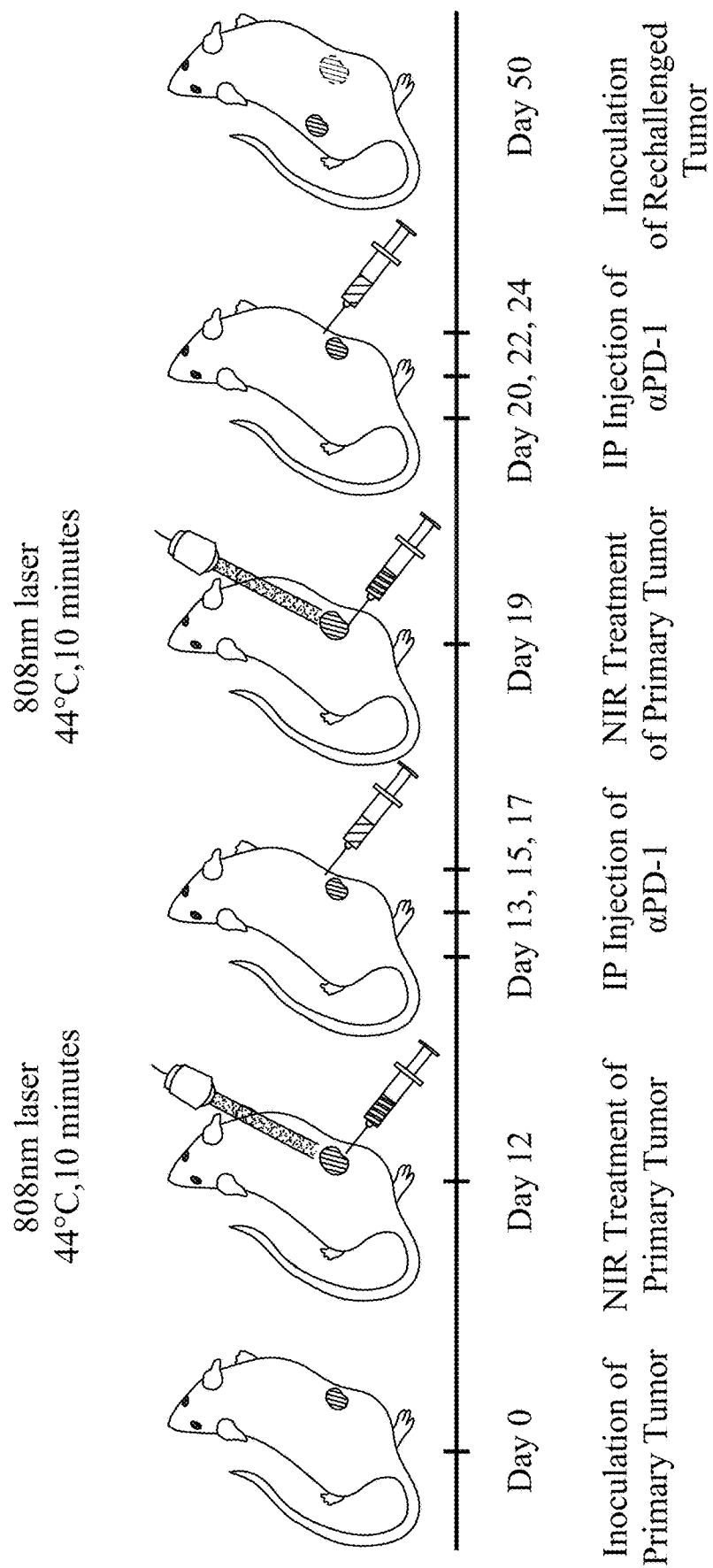
FIG. 9 is a schematic diagram showing time course of a treatment regimen using a kit for treating cancer of the present disclosure.

To assess the synergistic effects of in situ vaccination, which is mediated by heat-treated spiky metal organic framework, and the checkpoint blockade, which is induced by αPD-1, on the suppression of the growth of primary tumor and its efficacy against rechallenged tumor. Please refer to FIG. 9, which is a schematic diagram showing time course of a treatment regimen using the kit for treating cancer of the present disclosure. On Day 0, Balb/c mice are subcutaneously inoculated with $1\times10^6$ CT26 cells in their right flanks to generate primary tumor. Twelve days later, when the tumors had reached sizes of approximately 150 mm$^3$, the Balb/c tumor mice are treated intratumorally injected with Example 1, and then irradiated the tumor site of the Balb/c tumor mice with 808 nm NIR laser with a power density of 1.0 W/cm$^2$ for 10 minutes. On Days 13, 15, and 17, the Balb/c tumor mice are intraperitoneally injected with aPD-1. This treatment is repeated once on Day 7 after the beginning of the first cycle of treatment (hereinafter referred to as "Example 4"). The Balb/c tumor mice that had been only treated with PBS (hereinafter referred to as "PBS"), treated with PBS and then irradiated with 808 nm NIR laser (hereinafter referred to as "PBS+NIR"), only treated with Example 1 (hereinafter referred to as "Example 1"), only treated with aPD-1 (hereinafter referred to as "aPD-1"), treated with Example 1 and then irradiated with 808 nm NIR laser (hereinafter referred to as "Example 2") or treated with Example 1 and aPD-1 (hereinafter referred to as "Example 3") served as controls.

Figure 10A:
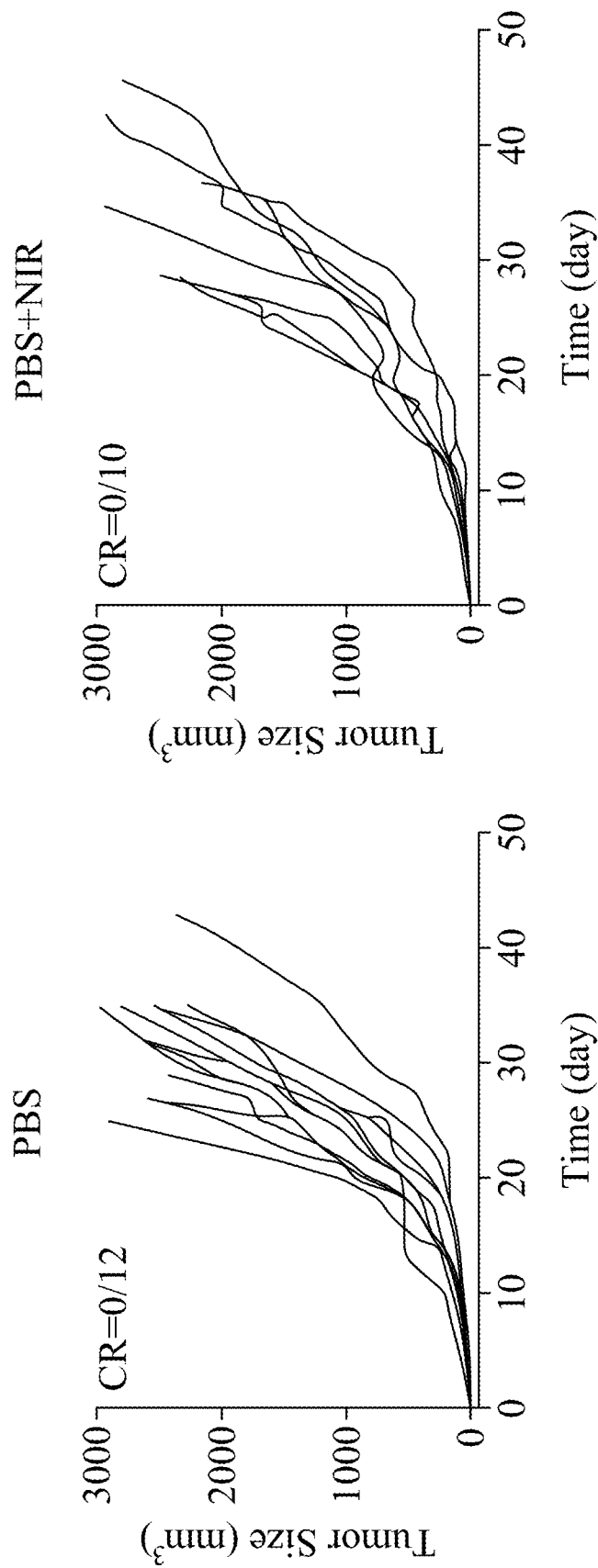
FIGS. 10A, 10B, 10C and 10D show first tumor growth curves of different treatment groups.
Figure 10B:
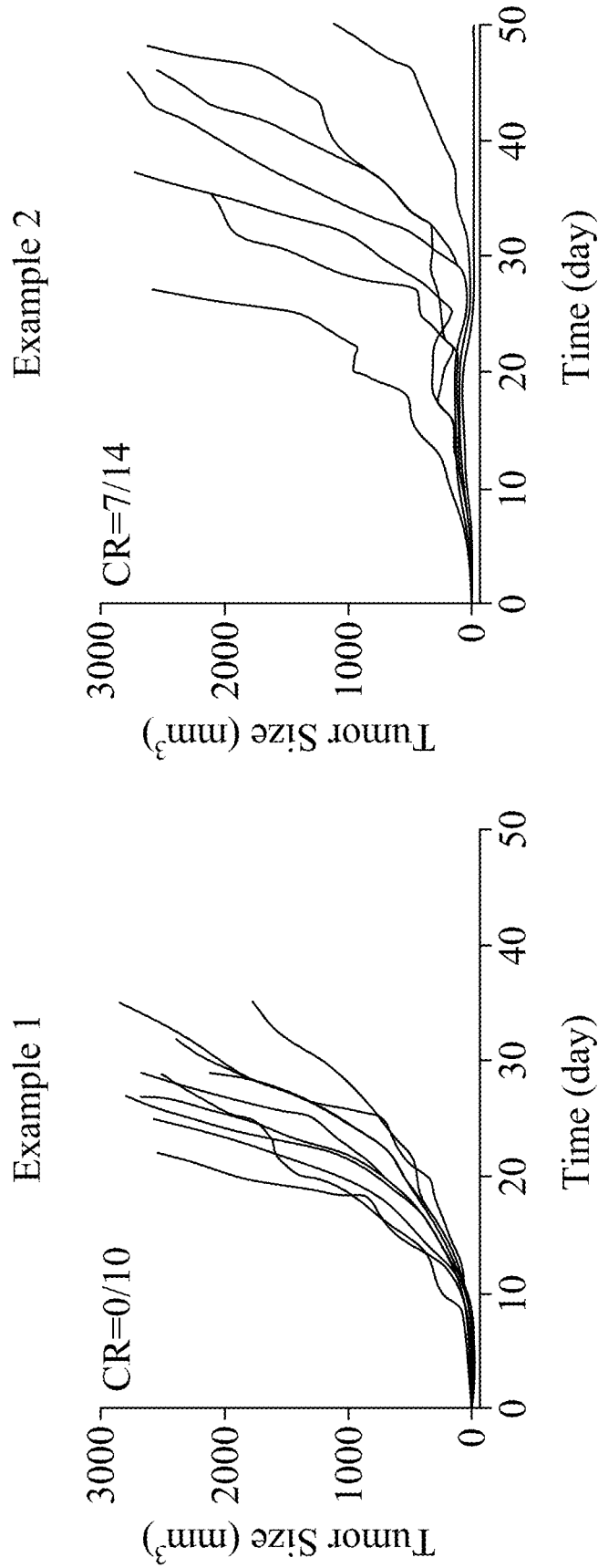
Figure 10C:
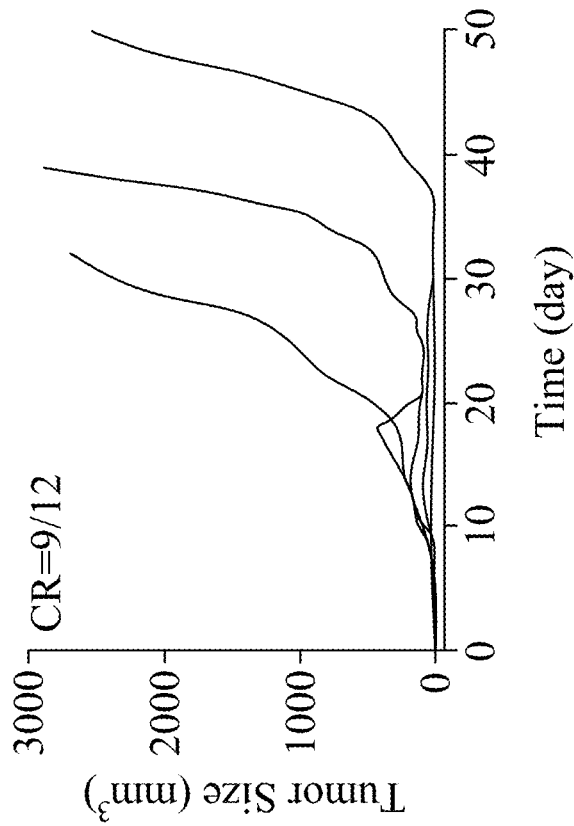
Figure 10C:
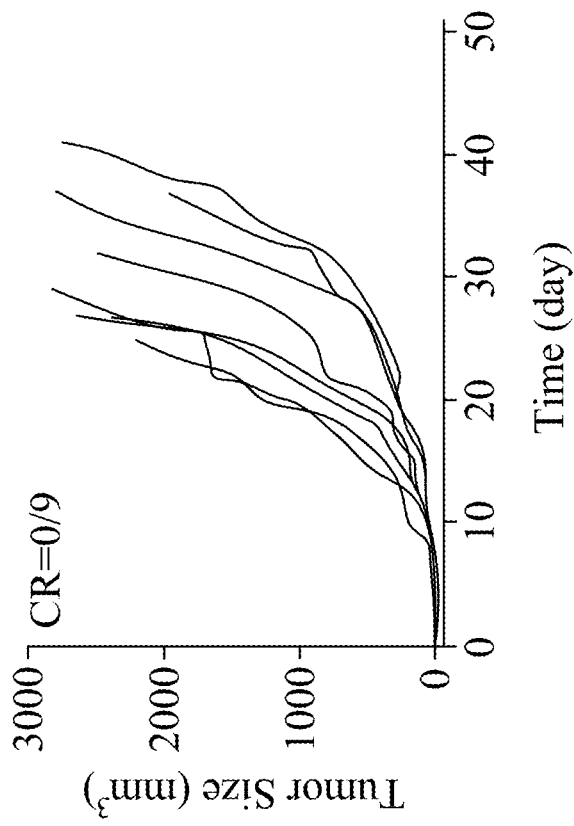
Figure 10D:
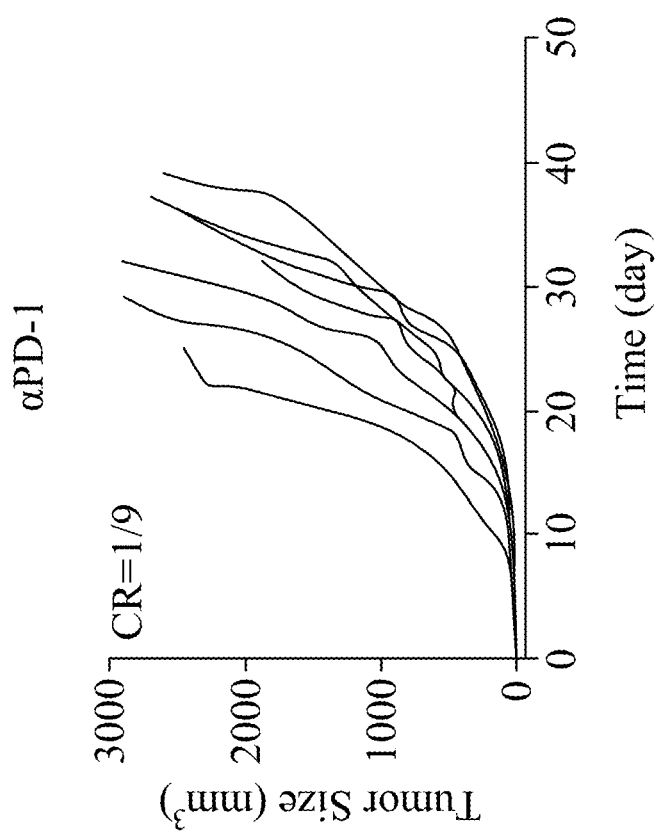
Figure 10E:
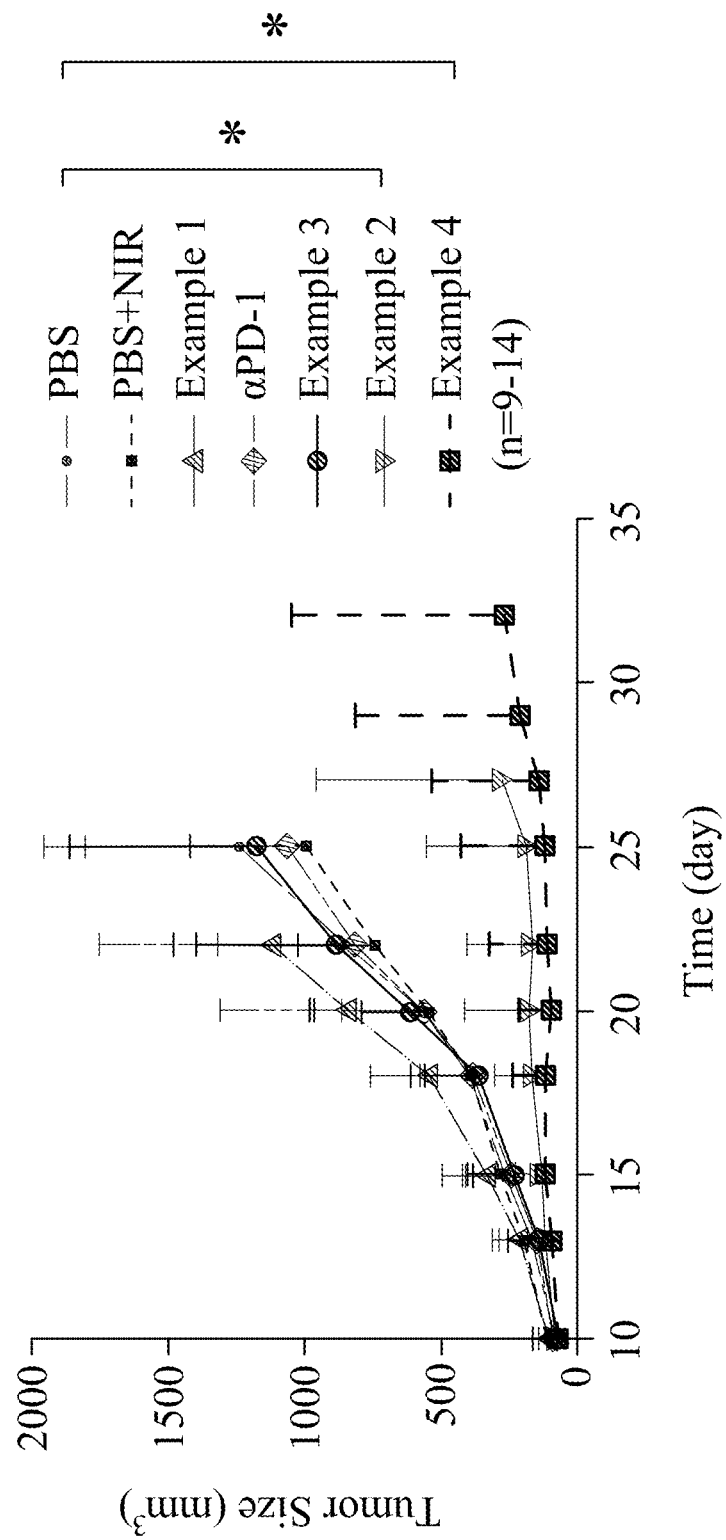
FIG. 10E shows an average tumor growth curve of each treatment group.
Figure 11:
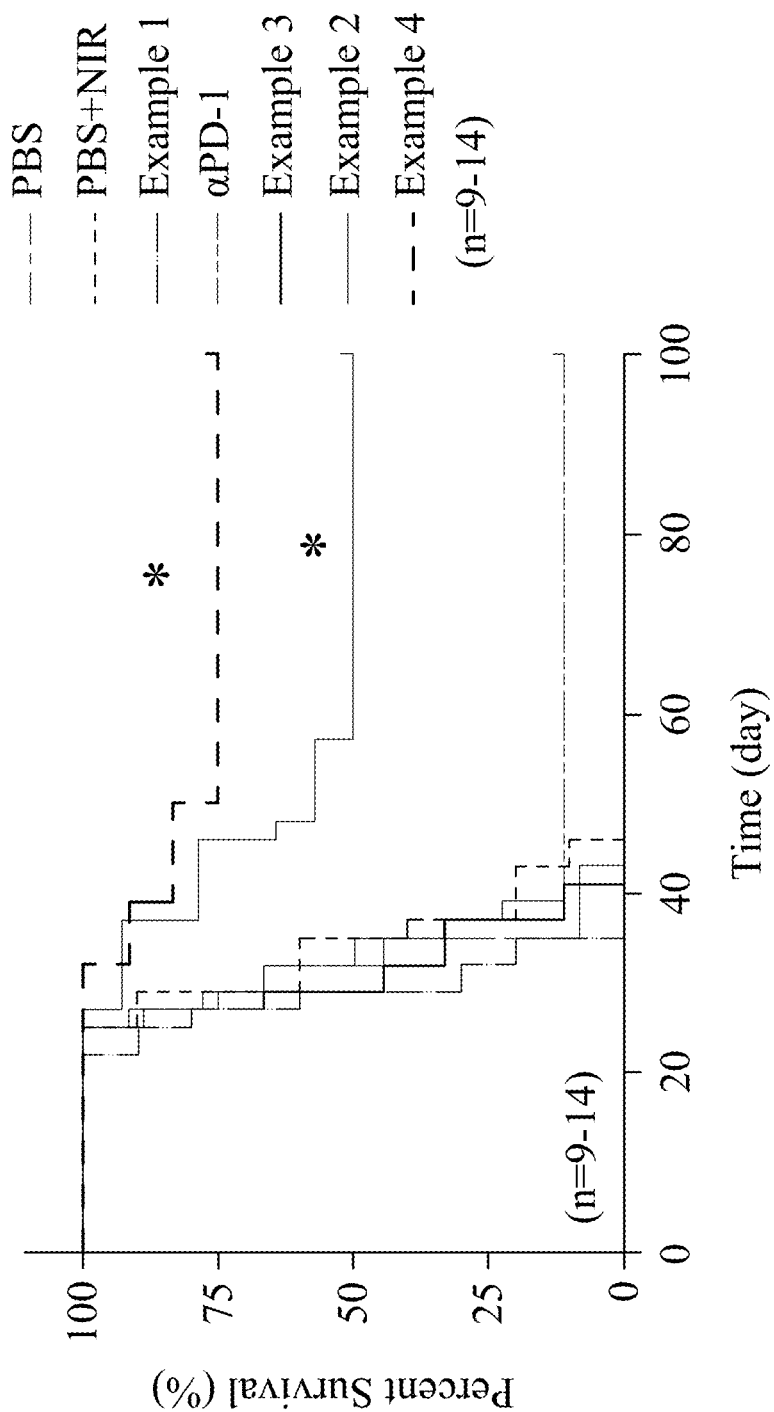
FIG. 11 shows a survival curve of each treatment group.

Please refer to FIGS. 10A, 10B, 10C, 10D, 10E and 11. FIG. 10A shows tumor growth curves of PBS group and PBS+NIR group, FIG. 10B shows tumor growth curves of Example 1 and Example 2, FIG. 10C shows tumor growth curves of Example 3 and Example 4, FIG. 10D shows tumor growth curves of aPD-1 group, FIG. 10E shows an average tumor growth curve of each treatment group, and FIG. 11 shows a survival curve of each treatment group.

In FIGS. 10A to 11, with respect to the inhibition of the growth of primary tumor, the Balb/c tumor mice that had been treated with PBS+NIR, Example 1, aPD-1, or Example 3 do not differ significantly from those treated with PBS (P>0.05), suggesting that these treatments are too weak to cause the regression of primary tumors. However, in situ vaccination with Example 2 significantly inhibit the growth of tumor (P<0.05), resulting in complete regression of the primary tumor and long-term (more than 50 days) survival in 50% of the Balb/c tumor mice, while the combination treatment with in situ vaccination and checkpoint inhibitor (Example 4) yield an even greater rate of tumor rejection, with complete regression in, and the survival of, 75% of the Balb/c tumor mice.

To evaluate further the long-term antitumor immunity that is induced by the kit for treating cancer of the present disclosure, surviving animals (mice that had survived the initial challenge), that are treated with the kit for treating cancer of the present disclosure (Example 2 and Example 4), are rechallenged with $1\times10^5$ CT26 cells subcutaneously in their left flanks on Day 50. The control group is a new batch of Balb/c mice, which only subcutaneously inoculated CT26 cells on the left side to generate a second tumor.

Figure 12:
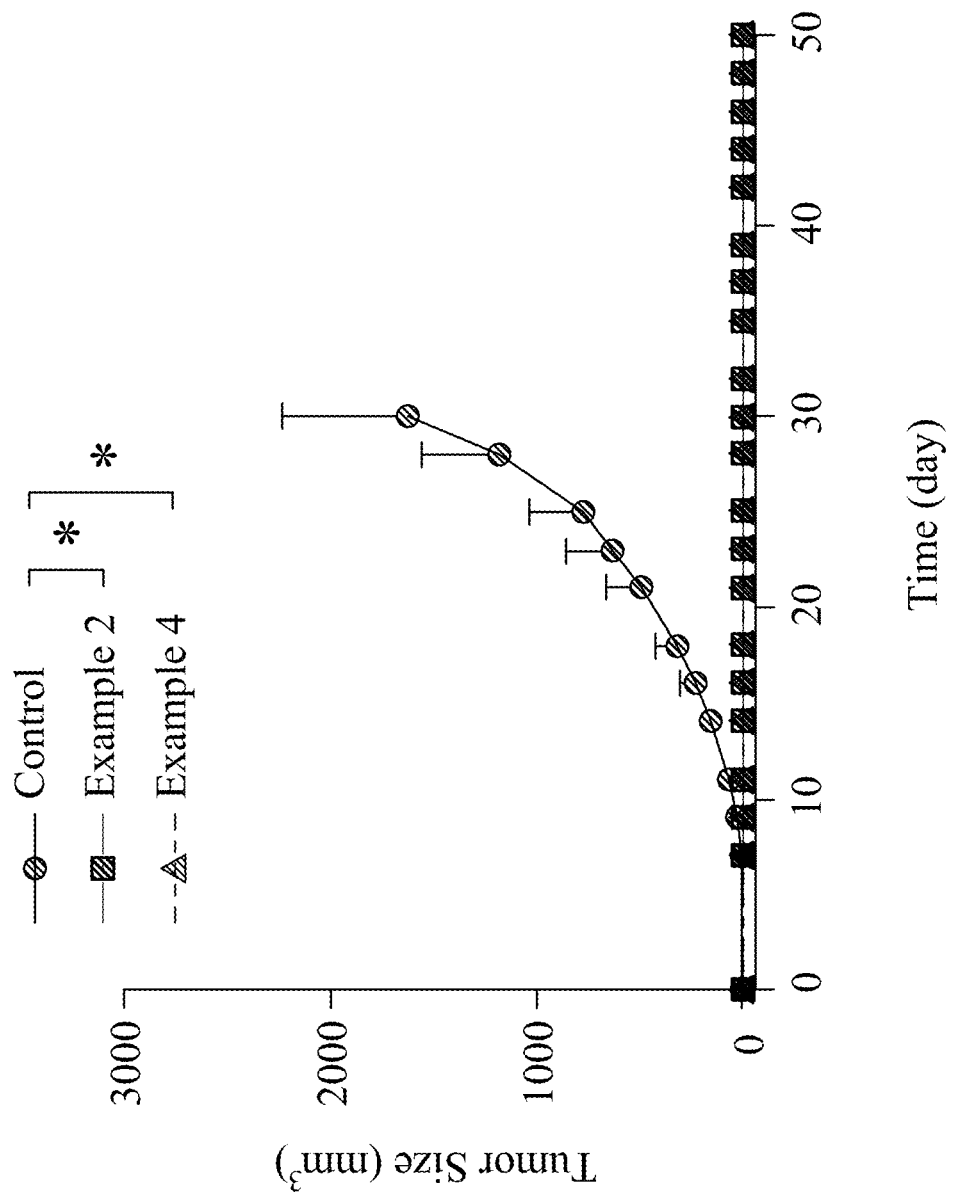
FIG. 12 shows a tumor growth curve of the second tumor of Balb/c tumor mice after treatment.

Please refer to FIG. 12, which shows a tumor growth curve of the second tumor of Balb/c tumor mice after treatment. In FIG. 12, all of the Balb/c tumor mice that had been treated with the kit for treating cancer of the present disclosure (Example 2 and Example 4) are completely resistant to rechallenge. These results suggest that the kit for treating cancer of the present disclosure (the spiky metal organic framework combined with heat therapy or the spiky metal organic framework combined with heat therapy and the immune checkpoint inhibitor) can strengthen anti-tumor immune memory responses in the Balb/c tumor mice, resulting in the effective prevention of cancer recurrence and metastasis.

Furthermore, the antigen-specific immune memory response that was induced by the kit for treating cancer of the present disclosure in the Balb/c tumor mice is examined using enzyme-linked immunospot (ELISPOT) assay. After the tumor is treated with the kit for treating cancer of the present disclosure, there will be a group of CD8$^+$ T lymphocytes with memory for tumor antigens in the spleen cells. When stimulated by the tumor antigen again, this group of cells will rapidly activate and secrete interferon-γ (IFN-γ), ELISPOT assay can be used to detect the presence of this group of cells. The Balb/c tumor mice whose tumors were completely healed after treatment with the kit for treating cancer of the present disclosure (Example 2 and Example 4)

were sacrificed, and their spleen tissues were harvested. The spleen tissues were grinded and filtered with 40 μm Cell Strainer to remove the residue, and then use ACK Lysing Buffer to dissolve and remove the red blood cells. The isolated lymphocytes and AH1 peptide (SPSYVYHQF) expressed by CT26 cells are co-cultured for 24 hours. Then ELISpot Mouse IFN-γ kit (R&D Systems) is used to detect the number of $CD8^+$ T lymphocytes secreting IFN-γ after stimulation. Finally, the results are analyzed by C.T.L. ImmunoSPOT Analyzer (Cellular Technology, Ohio, USA). The Balb/c mice of the same age that have not undergone other tests will serve as the control group for this test.

Figure 13:
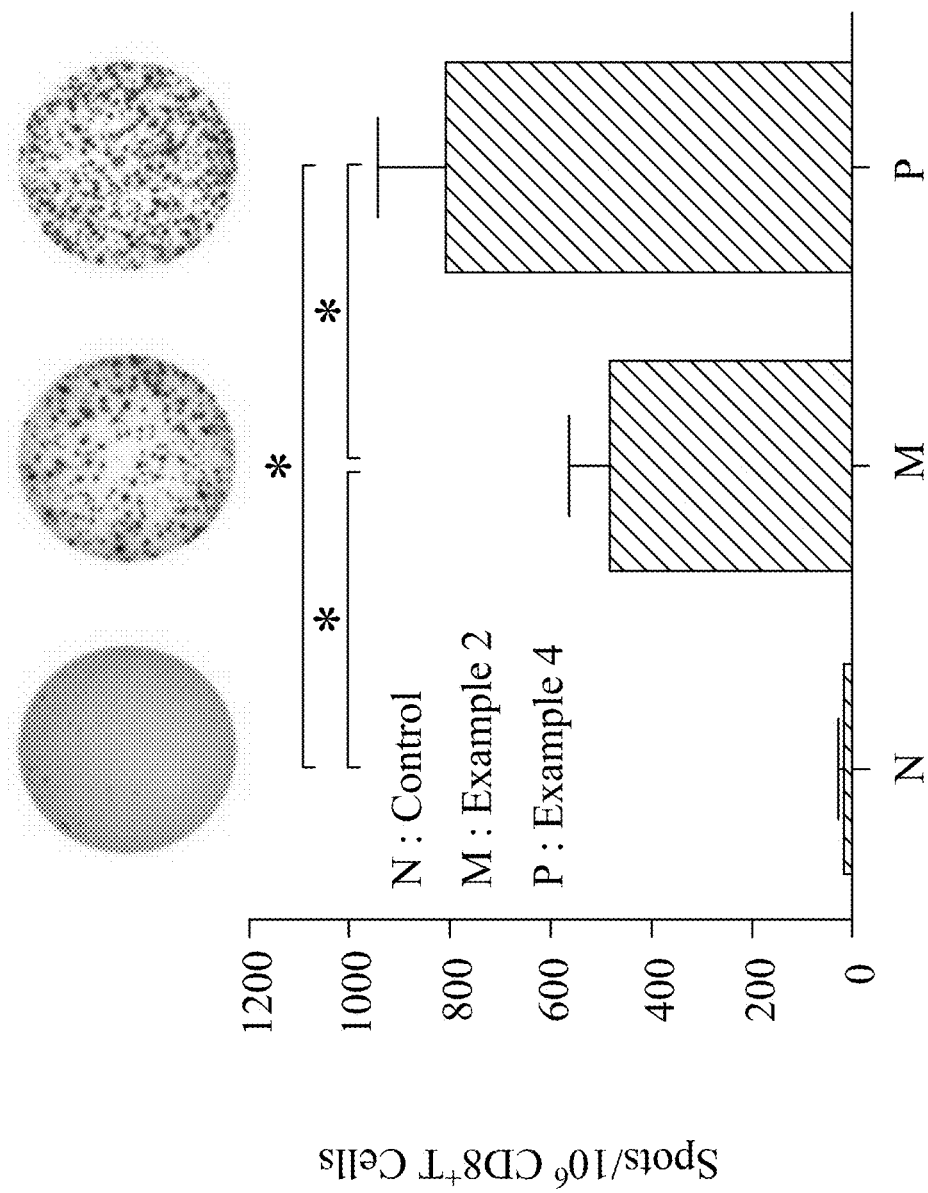
FIG. 13 shows analytical results of enzyme-linked immunospot method of the Balb/c tumor mice after treatment.

Please refer to FIG. 13, which shows analytical results of enzyme-linked immunospot method of the Balb/c tumor mice after treatment. In FIG. 13, the Balb/c tumor mice treated with the kit for treating cancer of the present disclosure indeed have lymphocytes that are immune to tumor-specific peptides. The Balb/c tumor mice treated with Example 2 and Example 4 yield dramatically more IFN-γ$^+$ spots than observed in the control group (P<0.05). The results indicate that the kit for treating cancer of the present disclosure can effectively induce systemic T-cell activation, increasing the number of tumor-specific $CD8^+$ effector cells in the Balb/c tumor mice, resulting in anti-tumor immune memory responses in the Balb/c tumor mice.

The ultimate goal of cancer immunotherapy is to recruit T cells into the tumor microenvironment and to activate them. After they are activated, tumor-infiltrating T cells can release cytoplasmic granules that contain granzyme B and perforin, killing the tumor cells. It is speculated that the kit for treating cancer of the present disclosure can change the tumor microenvironment to achieve such an excellent cancer treatment effect. Therefore, the infiltration of T cells in the local tumor microenvironment of the Balb/c tumor mice after treatment is further explored.

To assess the ability of each treatment modality to recruit T cells, the Balb/c tumor mice on the Day 7 after the first treatment are sacrificed, and histological sections and staining are performed. H&E staining is used to observe the changes of the tumor after treatment, and the In Situ Cell Death Detection Kit (TUNEL assay, Roche, Mannheim, Germany) is used to evaluate whether the treatment would promote the apoptosis of tumor cells in the Balb/c tumor mice. Sections are also stained with anti-mouse CD3 antibody, anti-granzyme B antibody for labeling the immune cells CD3 T lymphocytes in the tumor and the granzyme B secreted by them. Then sections are stained with DAPI to label the position of the nucleus. Finally, Zeiss LSM 780 is used to observe the infiltration of immune cells in the tissue and capture images.

Figure 14:
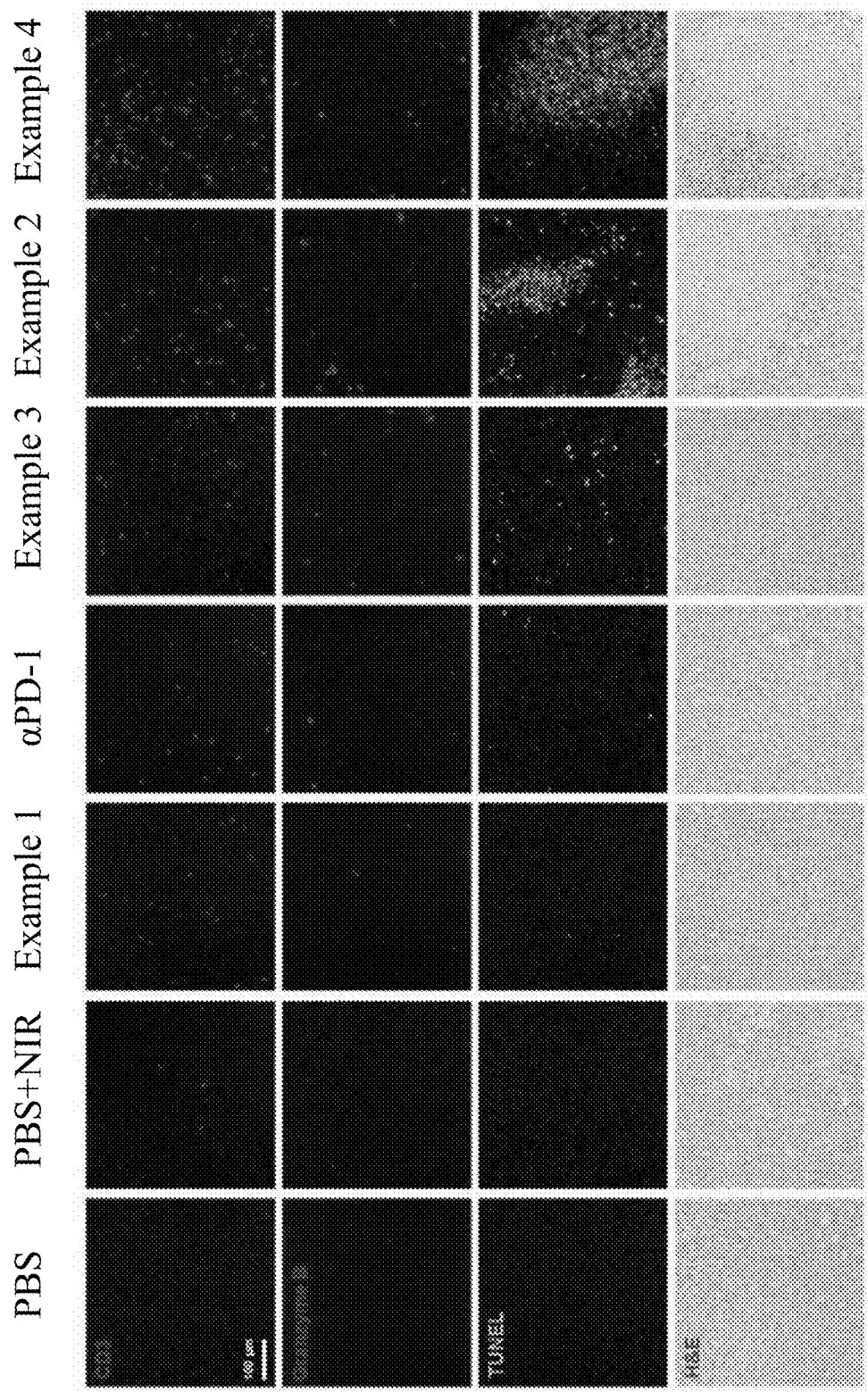
FIG. 14 shows analytical results of T cell infiltration in the local tumor microenvironment of the Balb/c tumor mice after treatment.

Please refer to FIG. 14, which shows analytical results of T cell infiltration in the local tumor microenvironment of the Balb/c tumor mice after treatment. The results show that the Balb/c tumor mice treated with the kit for treating cancer of the present disclosure (Example 2 and Example 4) can effectively induce apoptosis, attract more $CD3^+$ T lymphocytes and secrete more granzyme B. Therefore, the kit for treating cancer of the present disclosure can achieve such an excellent cancer treatment effect. In addition, the number of $CD3^+$ T cells and the expression of granzyme B in the tumor microenvironment in the group treated with Example 2 are higher than that of other control groups. The treatment of Example 4 further increases the infiltration/activation of T cells and modulates the immunosuppressive tumor microenvironment, resulting in tumor shrinkage and tumor cell death.

To evaluate the potential toxicity of the kit for treating cancer of the present disclosure, a series of in vivo experiments are performed. The body weights of treated Balb/c tumor mice are measured. At the end of the treatment program, sacrifice the Balb/c tumor mice after treatment, and histological sections of their major organs (spleen, liver, kidney, lung and heart) are examined. Sera from the Balb/c tumor mice that had received Example 2 or Example 4 are collected on Day 7 and 49 after treatment to measure the levels of their aspartate transaminase (AST), alanine transaminase (ALT), and blood urea nitrogen (BUN) to evaluate potential liver and kidney toxicities.

Figure 15B:
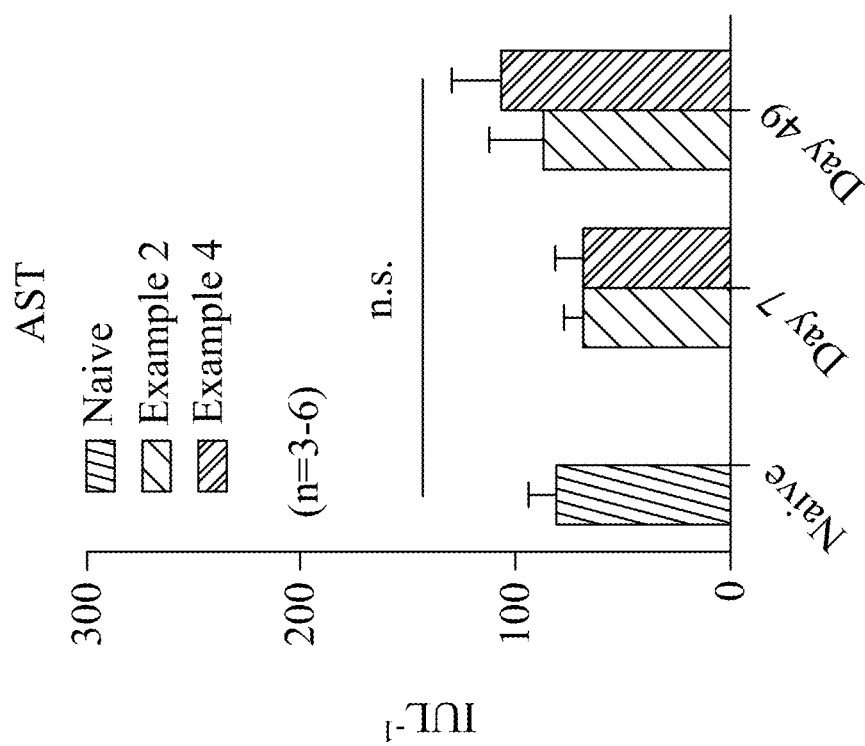
FIGS. 15B, 15C and 15D show analytical results of levels of AST, ALT and BUN in serum of the Balb/c tumor mice after treatment.
Figure 15C:
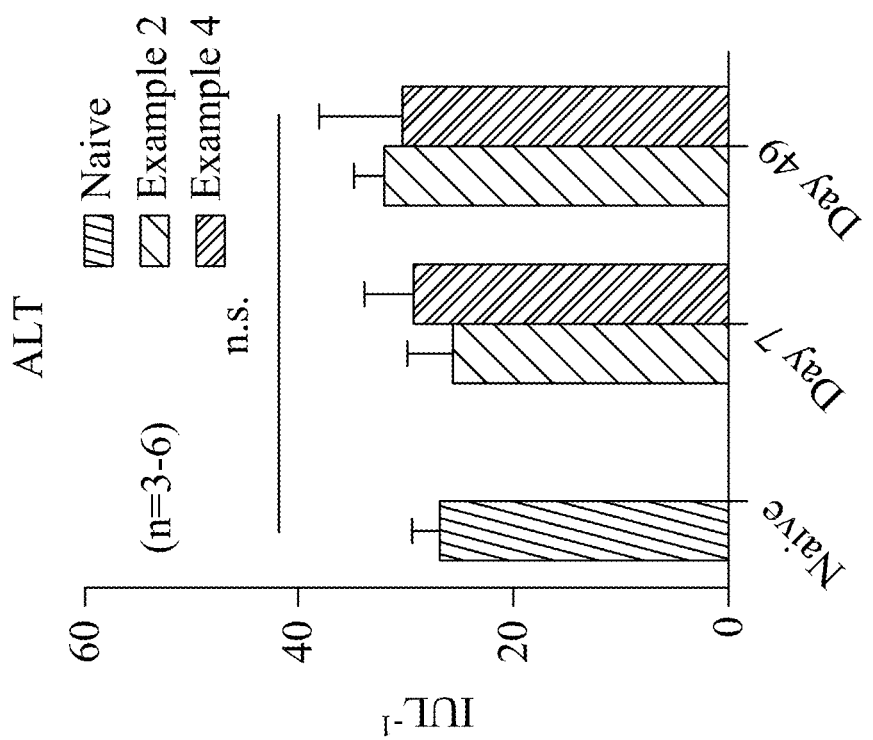
Figure 15D:
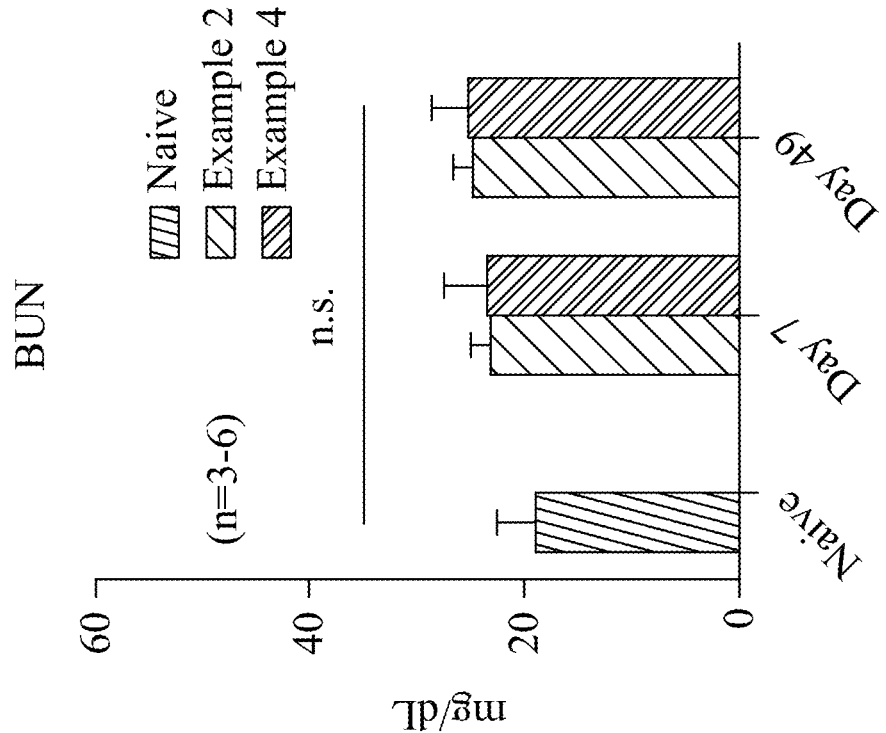
Figure 15E:
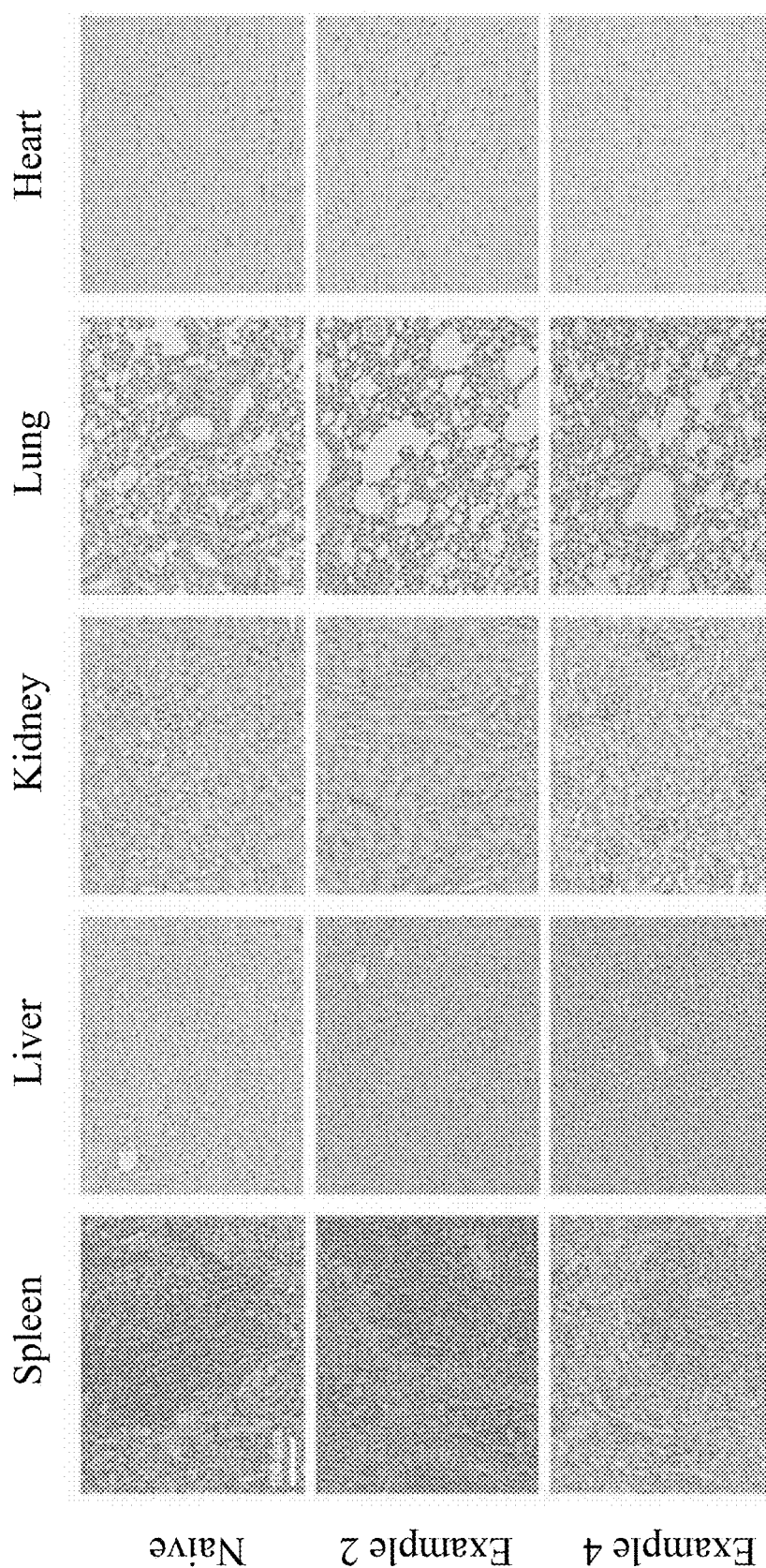
FIG. 15E shows the results of immunohistochemical staining of the spleen, liver, kidney, lung, and heart of experimental animals.

Please refer to FIGS. 15A, 15B, 15C, 15D and 15E. FIG. 15A shows weight curves of the Balb/c tumor mice in different treatment groups. FIGS. 15B, 15C and 15D show analytical results of levels of AST, ALT and BUN in serum of the Balb/c tumor mice after treatment. FIG. 15E shows the results of immunohistochemical staining of the spleen, liver, kidney, lung, and heart of experimental animals. In FIGS. 15A to 15E, treatment with Example 2 or Example 4 provoke neither an obvious loss of body weight nor abnormal changes in the levels of serum AST, ALT and BUN (P>0.05). No significant pathological changes in the spleen, liver, kidney, lung, and heart are observed. These experimental results show that the kit for treating cancer of the present disclosure generates hardly any in vivo toxicity.

Figure 16:
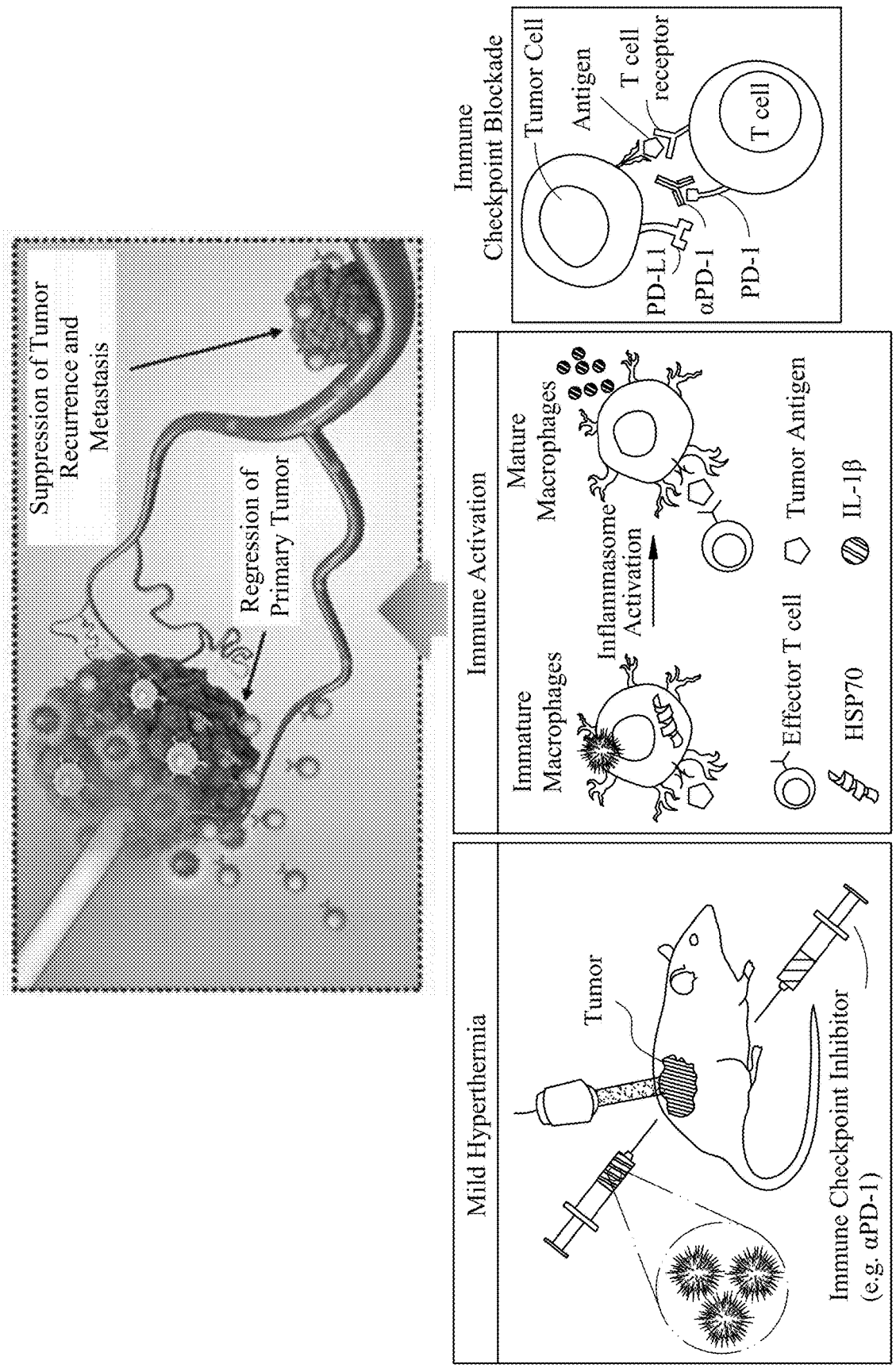
FIG. 16 is a schematic diagram showing an action mechanism of the kit for treating cancer of the present disclosure.

Please refer to FIG. 16, which is a schematic diagram showing an action mechanism of the kit for treating cancer of the present disclosure. The kit for treating cancer of the present disclosure can recruit immune cells to the host tumor microenvironment through the spiky metal organic framework imitating the structure of bacteria, and activate immune cell mechanism to convert a whole tumor into an in situ vaccine. Following the intratumoral injection of the spiky metal organic framework of the present disclosure into a tumor-bearing mouse model, the tumor is heat-treated using an NIR laser, mildly increasing its local temperature. Heat-treated tumors can recruit various immune cells, including APCs and effector T cells, to the location of the tumor. Furthermore, heat treatment can provide cell stress that increases antitumor immunity by modulating the local tumor microenvironment, including upregulating HSP70 to stimulate antitumor immune responses. Upon the uptake of the spiky metal organic framework by local APCs, the Al that is incorporated into the spiky metal organic framework can induce inflammasome activation in APCs and thereby improve their pro-inflammatory cytokine expression, ultimately activating the tumor-specific T cell responses that will generate systemic anti-tumor immunity. Therefore, the kit for treating cancer of the present disclosure can regress the primary tumor and the effectively inhibiting cancer recurrence and metastasis, greatly improving the efficiency of tumor treatment.

In summary, the spiky metal organic framework of the present disclosure can imitate the anti-tumor immune response of BMTT without causing adverse toxin side effects. When the spiky metal organic framework includes aluminum ion, the spiky metal organic framework of the present disclosure can be further used as an immune adjuvant. When the spiky metal organic framework includes ruthenium ion, the spiky metal organic framework of the present disclosure can be further used as a photothermal agent.

The kit for treating cancer of the present disclosure includes the spiky metal organic framework of the present disclosure and a light source device. The spiky metal organic framework can be irradiated by the light source device to absorb light energy to generate heat energy and maintain a relatively mild temperature. The heat energy makes the spiky metal organic framework have the dual effects of heat therapy and immunotherapy at the same time, and produces a synergistic therapeutic effect, which greatly improves the efficiency of tumor treatment. In addition, the kit for treating cancer of the present disclosure can improve the microenvironment of the tumor, attract the accumulation of CD3 T lymphocytes and secrete granzyme B, can cause the long-acting anti-tumor immune memory effect of the individual after treatment, and can prevent cancer recurrence and metastasis. Furthermore, if the kit for treating cancer further includes immune checkpoint inhibitor, which increases the infiltration/activation of T cells and modulates the immunosuppressive tumor microenvironment, resulting in a better cancer treatment effect. Therefore, the kit for treating cancer of the present disclosure is a potential form of cancer immunotherapy.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A spiky metal organic framework formed by a coordination reaction between at least one metal ion and an organic ligand, the spiky metal organic framework comprising:
    a body being a spherical shape, wherein a particle size of the body is 1 μm to 3 μm; and
    a plurality of spike-like structures, wherein the spike-like structures are distributed on a surface of the body, a diameter of each spike-like structure is 15 nm to 35 nm, and a length of each spike-like structure is 250 nm to 400 nm;
    wherein the at least one metal ion is aluminum ion, ruthenium ion, cobalt ion or iron ion, and the organic ligand is 2-aminoterephthalic acid or terephthalic acid.

2. A method for fabricating the spiky metal organic framework of claim 1, comprising:
    providing a mixed solution, wherein the mixed solution comprises the at least one metal ion, the organic ligand and a solvent, wherein the at least one metal ion is aluminum ion, ruthenium ion, cobalt ion or iron ion, and the organic ligand is 2-aminoterephthalic acid or terephthalic acid;
    performing a firing step, wherein the mixed solution is calcined at a calcining temperature for a calcining time to obtain the spiky metal organic framework, the calcining temperature is 160° C. to 200° C., and the calcining time is 8 hours to 24 hours; and
    collecting the spiky metal organic framework.

3. The method of claim 2, wherein the at least one metal ion is aluminum ion and ruthenium ion, and a mole ratio of the aluminum ion to the ruthenium ion is 2:3 to 6:1.

4. The method of claim 2, wherein the solvent is N,N-dimethylformamide (DMF), water, methanol or ethanol.

5. A kit for treating cancer, comprising:
    the spiky metal organic framework of claim 1; and
    a light supply device for irradiating the spiky metal organic framework.

6. The kit for treating cancer of claim 5, wherein a light source of the light supply device is ultraviolet light (UV), near infrared light (NIR), far infrared light (FIR) or visible light (VIS).

7. The kit for treating cancer of claim 5, further comprising an immune checkpoint inhibitor.

8. The kit for treating cancer of claim 7, wherein the immune checkpoint inhibitor is PD-1 antibody, PD-L1 antibody or CTLA-4 antibody.

* * * * *